United States Patent
Chiu et al.

(10) Patent No.: US 12,103,007 B2
(45) Date of Patent: Oct. 1, 2024

(54) BASE MODULE AND TRAY INSERT OF A MULTIPURPOSE TRAY FOR AN AUTOMATED PROCESSING SYSTEM, MULTIPURPOSE TRAY FOR AN AUTOMATED PROCESSING SYSTEM, AND METHOD OF SIMPLIFIED LOADING/UNLOADING OF A MULTIPURPOSE TRAY INTO/FROM AN AUTOMATED PROCESSING SYSTEM

(71) Applicant: Roche Molecular Systems, Inc., Pleasanton, CA (US)

(72) Inventors: Lawrence Chiu, Lucerne (CH); Ion Iordanoaia, Rotkreuz (CH); Reiner Hitt, Sursee (CH); Vijay Namasivayam, Lucerne (CH); Eduard Nawrocki, Bonaduz (CH); Michael Neugebauer, Filzbach (CH); Tim Moulton, Newport, RI (US); Sam Palmer, Arlington, MA (US); Gerd Schmieta, Boston, MA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 648 days.

(21) Appl. No.: 16/758,837

(22) PCT Filed: Oct. 18, 2018

(86) PCT No.: PCT/EP2018/078582
§ 371 (c)(1),
(2) Date: Apr. 23, 2020

(87) PCT Pub. No.: WO2019/081345
PCT Pub. Date: May 2, 2019

(65) Prior Publication Data
US 2021/0178398 A1    Jun. 17, 2021

Related U.S. Application Data

(60) Provisional application No. 62/575,727, filed on Oct. 23, 2017.

(51) Int. Cl.
*B01L 9/06* (2006.01)
*C12M 3/00* (2006.01)

(52) U.S. Cl.
CPC .............. *B01L 9/06* (2013.01); *C12M 23/48* (2013.01); *B01L 2200/023* (2013.01);
(Continued)

(58) Field of Classification Search
None
See application file for complete search history.

(56) References Cited

U.S. PATENT DOCUMENTS 3,778,232 A * 12/1973 McMorrow, Jr. ...... G01N 33/80
422/65
5,375,716 A    12/1994 Rubin et al.
(Continued)

FOREIGN PATENT DOCUMENTS

CN    102965273 A    3/2013
CN    103611594 A    3/2014
(Continued)

OTHER PUBLICATIONS

International Search Report; PCT/EP2018/078582; dated Mar. 26, 2019.

*Primary Examiner* — Paul S Hyun
(74) *Attorney, Agent, or Firm* — Maneesh Gupta

(57) ABSTRACT

The present invention describes a base module (100) and a tray insert (200, 300, 400) of a multipurpose tray (100) for an automated processing system, such as an analytical, pre-analytical or post-analytical processing system, as well as to a multipurpose tray comprising such base module and
(Continued)

such tray insert, wherein the tray insert can be particularly used for holding a plurality of reagent or sample tubes to be processed in the automated processing system. The present invention further relates to a method of simplified loading/unloading of such a multipurpose tray into/from the automated processing system.

14 Claims, 13 Drawing Sheets

(52) U.S. Cl.
CPC ..... *B01L 2200/028* (2013.01); *B01L 2200/16* (2013.01); *B01L 2300/0806* (2013.01)

(56) References Cited

U.S. PATENT DOCUMENTS

| | | | |
|---|---|---|---|
| 5,589,137 | A | 12/1996 | Markin et al. |
| 6,098,819 | A | 8/2000 | Link |
| 6,875,405 | B1* | 4/2005 | Mathus ............. B01L 9/06 422/549 |
| 8,142,740 | B2 | 3/2012 | Self et al. |
| 9,156,598 | B2 | 10/2015 | Nicoletti |
| 9,636,680 | B2 | 5/2017 | Fattinger et al. |
| 9,862,519 | B2 | 1/2018 | Deutschle et al. |
| 10,048,284 | B2 | 8/2018 | Müller et al. |
| 10,175,259 | B2 | 1/2019 | Riether |
| 10,654,041 | B2 | 5/2020 | Knight |
| 2003/0129095 | A1 | 7/2003 | Farina et al. |
| 2005/0194333 | A1* | 9/2005 | Veiner ............... G01N 35/04 211/74 |
| 2009/0026107 | A1* | 1/2009 | Ross ............... A61M 5/008 206/570 |
| 2009/0136386 | A1* | 5/2009 | Duffy ............. F16K 99/0032 422/400 |
| 2010/0266457 | A1 | 10/2010 | Rethwisch et al. |
| 2012/0149059 | A1 | 6/2012 | Shah |
| 2013/0061693 | A1 | 3/2013 | Sasaki et al. |
| 2015/0122693 | A1 | 5/2015 | Deutschle et al. |
| 2015/0344179 | A1 | 12/2015 | Riff et al. |
| 2015/0362515 | A1 | 12/2015 | Buse et al. |
| 2017/0136467 | A1 | 5/2017 | Johns et al. |

FOREIGN PATENT DOCUMENTS

| | | | |
|---|---|---|---|
| EP | 0415307 | A2 | 3/1991 |
| EP | 2098296 | A1 | 9/2009 |
| EP | 3139175 | A1 | 3/2017 |
| JP | 2002346966 | A | 12/2002 |
| JP | 2003095270 | A | 4/2003 |
| JP | 2005082240 | A | 3/2005 |
| JP | 2011148897 | A | 8/2011 |
| WO | WO2011135085 | A1 | 11/2011 |
| WO | 2011148897 | A1 | 12/2011 |
| WO | WO2017081410 | A1 | 5/2017 |
| WO | 2017146893 | A1 | 8/2017 |

* cited by examiner

BASE MODULE AND TRAY INSERT OF A MULTIPURPOSE TRAY FOR AN AUTOMATED PROCESSING SYSTEM, MULTIPURPOSE TRAY FOR AN AUTOMATED PROCESSING SYSTEM, AND METHOD OF SIMPLIFIED LOADING/UNLOADING OF A MULTIPURPOSE TRAY INTO/FROM AN AUTOMATED PROCESSING SYSTEM

CROSS-REFERENCES TO RELATED APPLICATIONS

This application is a national stage application, filed under 35 U.S.C. § 371, of International Patent Application No. PCT/EP2018/78582, filed Oct. 18, 2018, which claims the benefit and priority of U.S. Provisional Patent Application No. 62/575,727, filed Oct. 23, 2017, both of which applications are incorporated herein by reference

TECHNICAL FIELD

The present invention relates to a base module and a tray insert of a multipurpose tray for an automated processing system, such as an analytical, pre-analytical or post-analytical processing system, as well as to a multipurpose tray comprising such base module and such tray insert. The present invention further relates to a method of simplified loading/unloading of such a multipurpose tray into/from the automated processing system. In further detail, the present invention is directed to a base module of such a multipurpose tray, which base module receives the tray insert and forms the multipurpose tray together with the tray insert, wherein the tray insert can be particularly used for holding a plurality of reagent or sample tubes to be processed in the automated processing system. Based thereon, a method of simplified loading/unloading such a multipurpose tray into/from the automated processing system by an operator can also be achieved, as a side aspect of the present invention.

BACKGROUND

In laboratory settings, the processing of biological samples usually involves complex laboratory equipment and, thus, a complex workflow of operational steps carried out by laboratory personnel, such as a laboratory employee or a laboratory assistant, or the like. For example, such biological samples can entail human tissue, blood, saliva or urine, which samples are routinely taken from patients by medical personnel in hospitals or in private practice, for laboratory analysis, e.g. for determining concentration levels of different components within the taken samples. The complex workflow usually entails an increased number of procedural aspects to be considered ahead of the execution of each processing step, leading to a very time-consuming effort in addition to the processing steps themselves. Here, in order to counteract such time burden and comply with the usual time pressure of producing analysis results fast and reliable, any degree of automation of the largely manually carried-out process steps can significantly reduce personnel costs and increase sample throughput volume and, in turn, can reduce the time it takes to analyze the sample and report the results to the recipient.

Already available automated processing systems, e.g. for performing medical diagnostic analysis of biological samples, typically use already known commercially available sample containers for receiving the biological samples to be analyzed. Also, as addition to the biological samples, reagents can be required for the analysis, which reagents are usually provided in reagent containers. Such sample or reagent containers can come in the form of sample or reagent tubes, also referred to as primary tubes, or any other suitable kind of sample or reagent container which can be open at its top, or closed with a lid or the like, and which can differ slightly in shape and size. Furthermore, in order to facilitate the analysis process, it is common practice to use one particular kind of sample tube for a particular kind of sample, resulting in uniform sample containers for each type of sample, i.e. different kind of sample tubes for different kinds of sample, for the sake of streamlining the analyzing process and increasing sample throughput volume. The need to use different containers for different kinds of sample may also be dictated by various factors, such as sample volume, treatment conditions or the like, but—in any event—brings along the advantage that it is easier to tell different kinds of sample apart from each other, which makes it difficult to accidentally use the wrong kind of sample in a process intended for another kind of sample. This is particularly true where automated processing systems are used for processing the samples, since the automated systems usually comprise certain laboratory equipment designed for use with a certain kind of sample, i.e. with a certain kind of sample tube.

Now, in order to increase handling efficiency inside an automated processing system, such as an analytical, pre-analytical or post-analytical processing system, the sample or reagent tubes are usually placed into a tube tray adapted to support multiple tubes generally in an upright orientation. However, a laboratory usually receives the biological samples as well as the reagents in a lot of different tube types, wherein every tube type usually has its own tray adapted for the respective tube shape and size. This makes it complicated for an operator to load the laboratory processing system that treats different samples in different sample tube types. Also, in automated processing systems for processing biological samples, such as an analytical, pre-analytical or post-analytical processing system, the sample tubes are usually manipulated, for example by removing from or inserting into the tubes fluids or other specimen by means of a needle or pipette, or the like. Accordingly, handling the sample tubes generally requires a very exact positioning in relatively precise manner; otherwise, i.e. in case the sample tubes are not positioned with sufficient precision, a manipulator of such an automated processing system might not be in the position to reliably manipulate the sample tubes. Another problem of the trays is that their barcode is usually not human readable. Thus, the operator never knows if the samples are already treated, if they are fresh, or if the operator has to pay special attention, for example with infectious biological samples. A sample tube tray which can hold differently sized sample tubes and which is able to achieve the desired exact positioning can be gathered from, for example, U.S. Pat. No. 8,142,740 B2, in which a sample tube tray for an automated processing system is disclosed, which tray has several wells adapted to be able to hold one of two differently sized sample tubes in a concentric manner. As further known prior art, EP 2 098 296 A1 describes a sample tube tray for holding and positioning a plurality of sample tubes having outer diameters which lie within a predetermined diameter range. According to one particular embodiment of EP 2 098 296 A1, an improved sample tube tray is disclosed which can hold sample tubes with two different diameters, the tray basically consisting of uniformly spaced pillars. Accordingly, even though the known sample tube trays are usable for different sample tube designs, only fixed positions for the sample tubes can be used, i.e. it is not possible to merge smaller sample tubes closer together than bigger sample tubes.

Now, even though automated processing systems using the above described already known tube trays already improve sample processing efficiency by providing results more quickly while minimizing human error, there is the constant need for improvements in the overall performance of automated analyzer systems due to increasing demands on clinical laboratories regarding accuracy of analytical results and also sample throughput volume. In particular, the efficiency of patient sample handling continually needs to be increased, regardless of the assay to be performed. Here, the ability to quickly and securely introduce a plurality of samples or reagents into an automated processing system by means of sample or reagent tubes as described above is an important factor of achieving high efficiency in throughput of biological samples. In addition, the storing of different types of sample tubes or reagent tubes in one tray, the storing of several tube trays in small space, or the ability for laboratory personnel to carry several tube trays at once can highly increase the efficiency of patient sample handling with automated processing systems. Therefore, the constant need exists to improve the handling of a plurality of samples or reagents, of identical or mixed kind, in correlation with an automated processing system.

SUMMARY

The present invention addresses the above described problems and provides for a base module of a multipurpose tray, which base module receives at least one tray insert and forms the multipurpose tray together with the at least one tray insert, wherein the tray insert can be particularly used for holding a plurality of reagent or sample tubes to be processed in an automated processing system, such as an analytical, pre-analytical or post-analytical processing system. In particular, according to one aspect of the present invention, a base module of a multipurpose tray for such an automated processing system is provided, which base module is open on one side and comprises protrusions for engagement with at least one tray insert, wherein the at least one tray insert is releasably engagable within the open side of the base module by engagement with the protrusions of the base module. Accordingly, with the protrusions provided as integral part of the base module, at least one tray insert can be connected to the base module to form an engagement between the base module and the tray insert, or better between the open side of the base module and the tray insert, which engagement can be released again, if desired, in order to switch the tray insert with another tray insert of the same od a different kind, thereby rendering the tray to be a multipurpose tray. Accordingly, the multipurpose property of the multipurpose tray can already be achieved by the exchangeability of the tray insert, or also by the exchangeability of several tray inserts received by one and the same base module, for example in a mix and match manner, thereby achieving a high flexibility regarding the selection of tubes to be received by the multipurpose tray. Furthermore, as described further below in more detail, the multipurpose property of the multipurpose tray is also achieved by the ability of a tray insert according to the present invention to receive several different kinds of containers in one and the same tray insert, also referred to as universal tray insert.

According to a specific embodiment of the inventive base module of the presently described aspect, the protrusions of the base module, i.e. each protrusion provided integrally with the base module, protrudes laterally inward towards the inner side of the base module. Thereby, the protrusions of the base module can establish a form-fit connection in the form of a releasable push-in connection or a snap connection with respective counterparts of the tray insert, such as respective engagement features of the tray insert. For example, the protrusions of the base module can provide a kind of tongue of a tongue-and-groove connection, wherein respective engagement features of the tray insert provide the groove counterpart, for example by means of respective suitable engagement recesses. Here, for example, the protrusions can be of cylindrical shape, in order to match into respective circular engagement recesses in the tray insert. Alternatively or additionally, each cylindrical protrusion can comprise a center hole, open to the open side of the base module, which can receive a respective counterpart provided at the tray insert, such as a plug connector protruding from the bottom side of the tray insert, in order to be able to be pushed into the center hole of the respective protrusion of the base module, thereby establishing a push-in connection as mentioned above, which can be detached again. In general, regarding the manufacturing of a base module of the present invention, the base module can be an injection molded component, wherein the base module can be made of polypropylene (PP) or polycarbonate blends, such as polycarbonate with styrene acrylonitrile (PC/SAN) and polycarbonate with acrylonitrile-butadiene-styrene (PC/ABS), which all constitute injection-moldable materials.

According to a further specific embodiment of the inventive base module, the base module is stackable on top of another base module of a multipurpose tray of the same type. Thereby, several base modules can be stacked on top of each other in a space saving manner, independent from the tray insert provided in each of the stacked base modules, which also contributes to user convenience since several base modules can be stacked together when loaded with reagent or sample tubes provided by means of the respective tray insert and can be carried or transported in the stacked arrangement, thereby improving transportability and also storability of the base modules. In order to achieve such a stacking connection between at least two base modules on top of each other, the bottom side of each base module can comprise a step portion with reduced outer circumference, e.g. a narrowing step portion, which step portion matches into an upper edge of the open side of another base module. Accordingly, the step portion of the bottom side of the upper base module can be stacked into an upper edge of the open side of another base module, e.g. in a nestable manner.

Regarding the general structure of the inventive base module, the base module can comprise a rectangular structure with a substantially closed bottom side and at least partially closed side walls, usually four in number and thin-walled compared to the overall rectangular structure of the base module, wherein the upper side of the rectangular structure constitutes the above mentioned open side of the base module. With such structure, the base module constitutes a box shape with a substantially closed bottom, with the exception of manufacturing-related holes or slits or the like, side walls, which can be continuously closed or which can only be closed in part, and an open upper side, substantially without any kind of wall surface or the like. Regarding the structure of the side walls, at least one of the at least partially closed side walls of the base module can comprise an open side slot starting at the open upper side, i.e. the open upper side continues in the open side slot, and can continue toward the closed bottom side, wherein the side slot does not have to continue until the closed bottom side but can finish above the closed bottom, thereby constituting a window of the side wall open to the top.

According to an alternative specific embodiment, each side wall of the base module can comprise such an open side slot constituting a window of each side wall open to the top. Thereby, each corner of the rectangular structure comprises an angular corner post starting from the closed bottom and continuing to the open upper side, which angular corner posts can also be referred to as corner struts or corner pillars, achieving sufficient distance between the closed bottom side and the open side of the base module for receiving at least one tray insert as well as the tubes provided therein, without interacting with another base module stacked on top of it.

According to a further specific embodiment of the inventive base module, the base module comprises, as an interface, at least one handle on its outer circumference for improved transportability of the base module by an operator, such as laboratory personnel or the like, wherein the handle simplifies a grasping of the base module by the operator who can grasp the base module with one or two hands. Alternatively, the base module comprises, as an interface, two handles on its outer circumference opposite to each other, which even further improves the transportability of the base module by the operator, since the two opposite handles simplify a grasping of the base module by the operator who can grasp the base module with two hands.

According to a further specific embodiment of the inventive base module, the base module can comprise, as an interface, at least one engagement indentation on its outer circumference, wherein the engagement indentation is not to be confused by a handle as described above, but is particularly provided for a tray carrier, or tray carrier instrument such as a tray shuttle or the like, of the automated processing system, which carrier can engage with the indentation and, thus, pick up the base module, for improved transportability of the base module by the tray carrier in the course of an automated transportation process. For the sake of convenience, the at least one engagement indentation is provided within a handle positioned on the base module's outer circumference, as described above. Thereby, it becomes possible for the base module to be picked-up and transported not only by a human operator, but also by an automated tray carrier instrument, at the identical location at the base module. Similar to the provision of two handles as described above in an alternative embodiment, the base module can comprise, as an interface, two engagement indentations, or even more than two indentations, if necessary, on its outer circumference opposite to each other for improved transportability of the base module by the tray carrier of the automated processing system, wherein each engagement indentation can be provided within a handle allocated on the base module's outer circumference. Thereby, it becomes possible for the base module to be picked-up and transported not only by a human operator, but also by an automated tray carrier instrument in the same manner as being picked-up by a human operator with two hands, at the identical locations at the base module. The above described interfaces are provided as interfaces either form human interaction or as interface to instruments of an automated processing system, wherein the interfaces can be provided for interaction with such an instrument for the transport to and from loading slots of the automated processing system, to a work deck of the automated processing system, to a barcode labeler of the automated processing system, or for a tray shuttle provided within of the automated processing system.

According to a further specific embodiment of the inventive base module, the base module can comprise at least one color indicator for indication of a loading status of a content of the multipurpose tray, i.e. a content of the tray insert as received in the base module of the multipurpose tray. As one example, the color indicator can provide four different colors, which can indicate that the multipurpose tray has new, i.e. unprocessed, content, already processed content, content designated for the archive, or erroneous content, wherein the unprocessed content can be color-coded with green color and the already processed content, or alternatively erroneous content, can be color-coded with red color. Here, as a specific embodiment, the color indicator can be operable manually by the operator, and/or can be implemented in the form of a rotating indicator plug or pole provided in a respective pocket in the base module, for example in one of several corner posts of the base module, wherein the pocket comprises a viewing window to the outside, in which the respective color can be shown and changed by rotation of the indicator pole. Also, in case that the multipurpose tray carries content that is not in need of loading status indication, for example in case the tray insert carries consumable tips or the like, i.e. content without any status, a so-called blind plug can be fitted into the base module pocket, i.e. a plug without any different colors provided on it, such as a grey-colored plug or the like. Accordingly, the color indicator can be replaced, if desired, for improved user convenience. Furthermore, it is to be noted that the color indicator is particularly reasonable when using a so-called universal tray insert which can hold different kinds of sample tubes, or when using a urine sample container tray. On the other hand, a blind plug can be reasonable when using a consumable tips carrying tray insert, as mentioned before. As additional aspect of the provision of the indicator in form of an indicator pole stuck into a pocket of the base module, any optical sensor of the automated processing system can be used to identify the correct loading of the multipurpose tray into a loading slot of the automated processing system, since the pocket is either provided on the end of the tray loaded first into the loading slot, or not. Depending on the desired orientation of the tray when loaded into the loading slot, the correct orientation or a false orientation can be detected and, for example, signalized to an operator.

According to a further specific embodiment of the inventive base module, the base module can comprise at least one writable surface on its outer circumference, in order for an operator to provide the base module with a human readable marking and allowing rapid marking and erasing of such markings on the surface by a human operator, if desired, wherein the writable surface can be implemented by means of a whiteboard material, i.e. a wipeable material, to be able to use it more then one time. Thereby, any operator can provide the base module, and, thus, the multipurpose tray with human-readable markings, if desired, which can easily be erased again, for example when using the base module another time together with another tray insert, in order to write the content of the tray insert onto the base module. According to a one implementation of the writable surface, the same can be provided by means of the placement of a label on a side wall of the base module, for example the right side of the base module, wherein it is useful if the writable surface in the form of the label can only be cleaned with alcohol or suchlike, in order to improve the durability of the operator's markings. Thus, the writable surface provides white space to label the trays with notes for co-workers or co-operators, or the like, for example in order to prevent risk of loosing of delayed samples.

In addition to the human-readable marking as described before, the base module of the present invention can also comprise at least one identification code on its outer circumference, which can be an adhesive label or the like, carrying a human-readable machine-writing, which can provide substantial information about the base module or its content for a human operator. Alternatively or additionally, a machine-readable identification code can be provided on the outer circumference of the base module, for example implemented by a barcode or the like, or also in the form of a RFID tag or the like, which makes an automatic identification of the base module or its content in the automated processing system possible, and which can provide a unique identification code for each base module. For example, such barcode or RFID tag can consist of 3 characters for identification of the tray type, i.e. the type of tray insert provided in the base module, and 5 characters giving a consecutive serial number, for recordability reasons.

According to another aspect of the present invention, and in complementary addition to the base module as described above, a tray insert of a multipurpose tray for an automated processing system is provided herewith, for holding a plurality of reagent or sample tubes having similar or differing diameters, wherein the tray insert can also be referred to as universal tray insert or universally applicable tray insert and comprises an array of tube receiving recesses with different sizes, thereby achieving the universal property of the universal tray insert, wherein the size can be, for example, the tube receiving recess diameter, and tube receiving recesses can be formed in a substantial cylindrical shape. In general, regarding the manufacturing of such a tray insert of the present invention, the tray insert can be an injection molded component, wherein the tray insert can be made of polypropylene (PP) or polycarbonate blends, such as polycarbonate with styrene acrylonitrile (PC/SAN) and polycarbonate with acrylonitrile-butadiene-styrene (PC/ABS), which all constitute injection-moldable materials. Regarding the structure of the universal tray insert of the present invention, the above mentioned array of tube receiving recesses comprises at least a first group of tube receiving recesses, and also a second group of tube receiving recesses, wherein the size of a recess of the first group of tube receiving recesses and the size of a recess of the second group of tube receiving recesses differ from each other, i.e. the recess sizes between those groups are different to each other. For example, the first group of tube receiving recesses can be used for receiving a first group of tubes with a large diameter, and the second group of tube receiving recesses can be used for receiving tubes with a smaller diameter than the first group of tubes. Moreover, a contour of an inner circumference of each tube receiving recess of the first group of tube receiving recesses intersects with a contour of an inner circumference of at least one adjacent tube receiving recess of the second group of tube receiving recesses. Here, as contour of an inner circumference of a tube receiving recess, an outline of the inner circumference of the tube receiving recess is to be understood, wherein the contour or outline of the inner circumference of the tube receiving recess can also be identified as the substantial cross-section of the tube receiving recess when viewed from above. However, the inner circumferences of the tube receiving recesses of both the first group and the second group do not have to be continuous, wherein the tube receiving recesses of both groups can intersect with each other when viewed from above, thus exhibiting an intersection of the contour of an inner circumference of each tube receiving recess of the first group of tube receiving recesses with the contour of an inner circumference of at least one adjacent tube receiving recess of the second group of tube receiving recesses. With such a particular structure of tube receiving recesses with differing sizes, a universal tray insert design can be achieved which can receive different container shapes and sizes, wherein it particularly becomes possible to merge smaller containers closer together than bigger containers. Accordingly, different tube types with differing diameters can fit in the universal tray insert and, thus, in the respective multipurpose tray, always in an optimized way, in order to achieve an increase in receivable tube number that can be inserted into the universal tray insert. Thus, such a particular structure of tube receiving recesses results in the universal property of the universal tray insert, since the tray insert can be universally used for a plurality of different kinds of sample tubes. Here, as an example, in case only one type of tubes is loaded into the universal tray insert, it becomes possible to load about 20 pieces, such as 21 pieces of tubes with large diameter, such as PreservCyt tubes, or about 30 pieces, such as 32 pieces of tubes with a smaller diameter, such as SurePath tubes. In case different tubes are loaded, of the previously described kind, between about 20 and 30 pieces can be loaded in a mixed manner.

According to a further specific embodiment of the inventive tray insert, the intersection of contours of the first group of tube receiving recesses and the second group of tube receiving recesses corresponds to a non-tangential crossover of contours. This is to be understood in that the intersection point or junction point between the different contours, i.e. the contour of an inner circumference of each tube receiving recess of the first group of tube receiving recesses crosses the contour of an inner circumference of at least one adjacent tube receiving recess of the second group of tube receiving recesses in a non-tangential manner. This is particularly relevant when considering the cylindrical contours of each tube receiving recess, since such an arrangement specifically assists in achieving the optimized way of fitting tubes with differing diameters into the inventive tray insert, in order to achieve an increase in receivable tube number that can be inserted into the tray insert. Alternatively or additionally, a center axis of each respective tube receiving recess of the first group of tube receiving recesses can be arranged in an eccentric manner in relation to a center axis of an adjacent tube receiving recess of the second group of tube receiving recesses, meaning that the center axes of both groups of tube receiving recesses do not coincide with each other, which additionally assists in achieving the already described optimized way of fitting tubes with differing diameters into the inventive tray insert. Here, the distances between the respective axes are chosen so that a "wrong" loading of tubes into the universal tray insert is not possible, or at least can easily be detected by the operator during loading.

According to a further specific embodiment of the inventive tray insert, a depth of each tube receiving recess of the first group of tube receiving recesses is different from a depth of each tube receiving recess of the second group of tube receiving recesses. Thereby, tubes with differing length can also be received by the presently described tray insert, wherein it can be advantageous that the depth of the different groups of tube receiving recesses are chosen such that the tops of the one group of tubes having a longer length do not or only slightly protrude compared to the other group of tubes having a shorter length.

According to a further specific embodiment of the inventive tray insert, the array of tube receiving recesses comprises a third group of tube receiving recesses additionally to the already described first and second groups of tube receiving recesses, wherein a contour of an inner circumference of at least one of tube receiving recesses of the third group of tube receiving recesses intersects with a contour of an inner circumference of at least one adjacent tube receiving recess of the first and/or second group of tube receiving recesses. Accordingly, the array of tube receiving recesses comprises additionally a third group of tube receiving recesses, wherein the size of a recess of the third group of tube receiving recesses and the size of a recess of the first and/or second group of tube receiving recesses differ from each other, i.e. the recess sizes between those groups are different to each other. For example, the first group of tube receiving recesses can be used for receiving a first group of tubes with a large diameter, the second group of tube receiving recesses can be used for receiving tubes with a smaller diameter than the first group of tubes, and the third group of tube receiving recesses can be used for receiving a third group of tubed with an even smaller diameter than the second group of tubes. Moreover, a contour of an inner circumference of at least one of a of tube receiving recess of the third group of tube receiving recesses intersects with a contour of an inner circumference of at least one adjacent tube receiving recess of the first/second group of tube receiving recesses. Here again, as contour of an inner circumference of a tube receiving recess, an outline of the inner circumference of the tube receiving recess is to be understood, wherein the contour or outline of the inner circumference of the tube receiving recess can also be identified as the substantial cross-section of the tube receiving recess when viewed from above. However, the inner circumferences of the tube receiving recesses of all three groups do not have to be continuous, wherein the tube receiving recesses of all groups can intersect with each other when viewed from above, thus exhibiting an intersection of the contour of an inner circumference of each tube receiving recess of the first group of tube receiving recesses with the contour of an inner circumference of at least one adjacent tube receiving recess of the second group of tube receiving recesses and/or with the contour of an inner circumference of at least one adjacent tube receiving recess of the third group of tube receiving recesses. With such a particular structure of tube receiving recesses with differing sizes, the above mentioned universal tray insert design can be further improved in that it can receive three different container shapes or sizes, wherein it again becomes possible to merge smaller containers closer together than bigger containers. Accordingly, different tube types with three differing diameters can fit in the universal tray insert and, thus, in the respective multipurpose tray, always in an optimized way, in order to achieve an increase in receivable tube number that can be inserted into the universal tray insert. For example, in case only one type of tubes is loaded into the universal tray insert, it becomes possible to load about 20 pieces, such as 21 pieces of tubes with large diameter, such as PreservCyt tubes, about 30 pieces, such as 32 pieces of tubes with a smaller diameter, such as SurePath tubes, or about 80 pieces, such as 78 pieces of tubes with an even smaller diameter, such as PCR tubes. Thus, the array of tube receiving recesses can receive between about 20 and 80 sample tubes, of the same type or of different types in a mixed manner, depending on the respective diameter of the sample tubes and, thus, depending on the diameters of the tube receiving recesses. With an alternative arrangement of tube receiving recesses, 20 pieces of tubes with large diameter, such as PreservCyt tubes, 20 pieces of tubes with a smaller diameter, such as SurePath tubes, or 62 pieces of tubes with an even smaller diameter, such as PCR tubes can be loaded. Such a particular structure of tube receiving recesses results in further improvement of the universal property of the universal tray insert, since the tray insert can be universally used for an even bigger plurality of different kinds of sample tubes. As an additional optional feature, in order to achieve a further stabilized holding of any kind of sample tube, which makes it possible to also introduce smaller tubes into larger tube receiving recesses, a centering spring can be provided inside at least one of the tube receiving recesses, for centering a tube inside the respective tube receiving recess, i.e. for centering and holding a smaller tube inside a larger tube receiving recess. Accordingly, such a centering spring can further improve the universal property of the universal tray insert, since the tray insert can be universally used for an ever-greater plurality of different kinds of sample tubes. For example, a centering spring in accordance with the present invention can comprise a substantially circular middle part for attachment inside a tube receiving recess, and several clamp arms protruding away from the middle part in a longitudinal manner, each comprising an inwardly protruding nib at its end, for contacting the tube to be held, thereby holding and centering the same in coaxial manner with the centering spring, i.e. with the respective tube receiving recess, in a clamped manner. Such centering spring, as a separate component of the tray insert, can be made of spring steel, in order to improve its clampability, in addition to the clampability as achieved by the shape of the centering spring itself.

According to a further specific embodiment of the inventive tray insert, a center axis of each respective tube receiving recess of the third group of tube receiving recesses is arranged in an eccentric manner in relation to a center axis of an adjacent tube receiving recess of the first and/or second group of tube receiving recesses, meaning that the center axes of all groups of tube receiving recesses do not coincide with each other, which additionally assists in achieving the already described optimized way of fitting tubes with differing diameters into the inventive tray insert. Here, the distances between the respective axes are chosen so that a "wrong" loading of tubes into the universal tray insert is not possible, or at least can easily be detected by the operator during loading. Alternatively or additionally, a depth of each tube receiving recess of the third group of tube receiving recesses is different from a depth of each tube receiving recess of the first and/or second group of tube receiving recesses. Thereby, tubes with differing length can also be received by the presently described tray insert, wherein it can be advantageous that the depth of the different groups of tube receiving recesses are chosen such that the tops of one or two groups of tubes having a longer length do not or only slightly protrude compared to the remaining group of tubes having a shorter length. Moreover, a contour of each tube receiving recess of one group of tube receiving recesses can be spaced apart from a contour of an adjacent tube receiving recess of the same group of tube receiving recesses. Thus, a direct contact between the tubes of the same group of tubes can be avoided, thereby achieving a maximum exploitation of the space provided by the entire tray insert for this kind of tube.

According to a further specific embodiment of the inventive tray insert, fiducial markers are provided at the edge of an upper surface of the tray insert. The fiducial markers are used for clear allocation of each of the tube receiving recesses in the tray insert, wherein the fiducial markers can be provided in the form of a grid consisting of alphabetic characters and/or numbers, for identifying each tube receiving recess. Here, as an example, the individual positions can be printed on the edge of the tray insert in the form of a grid, such as known from a chessboard, wherein letters can assign rows and numbers can assign columns, for example from A1 to M11.

As already mentioned above, the tray insert comprises engagement features for being releasably engagable with protrusions within an open side of a base module of a multipurpose tray. As already described above in relation to the base module, the protrusions of the base module can provide a kind of tongue of a tongue-and-groove connection, wherein the respective engagement features of the tray insert provide the groove counterpart, for example by means of respective suitable engagement recesses which can be provided in an outer circumferential edge of the tray insert. Alternatively, the engagement features can be provided in the form of plug-in connectors provided on a bottom side of the tray insert, which connectors can be pushed into a center hole of the respective protrusions of the base module. In both cases, a push-in connection between the base module and the tray inset can be achieved, which can be detached again.

According to another aspect of the present invention, a multipurpose tray for an automated processing system is also provided by the present invention, which multipurpose tray comprises a base module as described above in detail, as well as at least one tray insert as described above in detail. Here, the tray insert can be enclosed at least in part by the base module in a framed manner without the at least one tray insert protruding to the outside of the base module. Also, as described above, the content of the tray insert does not protrude to the outside of the base module. Thereby, the stackability of the multipurpose tray can be achieved, independent the chosen tray insert and its content. Further, the protrusions of the base module and the engagement features of the tray insert establish a form-fit connection in the form of a releasable push-in connection or a snap connection, as already described above in detail.

Furthermore, in accordance with a further aspect of the present invention, a method of simplified loading/unloading of a multipurpose tray into/from an automated processing system by an operator is also provided. Such multipurpose tray can be the multipurpose tray as described above, or, alternatively, a multipurpose tray having any kind of tray insert inserted therein. Here, the inventive method comprises the steps of loading such a multipurpose tray into a loading slot, also referred to as input slot, of the automated processing system, wherein the automated processing system can comprise more than one loading slot; processing the content of the multipurpose tray by laboratory instrument of the automated processing system, such as an analytical instrument; and unloading the multipurpose tray from an unloading slot, also referred to as output slot, of the automated processing system, wherein the automated processing system can comprise more than one unloading slot. Here, the automated processing system comprises a sensor recognizing the content of the multipurpose tray loaded into the loading slot without interaction between the operator and software of the automated processing system, i.e. the automated processing system is able to automatically recognize the loaded multipurpose tray and its content by means of the sensor, such as an optical sensor, an RFID sensor or the like, and, thus, is able to identify the necessary or desired processing steps to be carried out automatically by the laboratory instruments inside the automated processing system, without the necessity for the operator of data input regarding the content of the multipurpose tray, for example by means of a user interface. Moreover, the multipurpose tray to be unloaded from the unloading slot of the automated processing system can be unloaded by the operator from the unloading slot without interaction between the operator and software of the automated processing system regarding the format or content of the multipurpose tray, i.e. the automated processing system allows unloading of the multipurpose tray without the necessity for the automated processing system to provide data about the multipurpose tray to be unloaded to the operator, for example by means of the user interface. However, in general, any multipurpose tray to be unloaded from the unloading slot of the automated processing system can only be unloaded by the operator from the unloading slot by interaction between the operator and software of the automated processing system, i.e. the automated processing system allows unloading of the multipurpose tray only with a respective input from the operator to the system, for example by means of the user interface. In general, the automated processing system can comprise a control unit carrying application software for interaction with an operator as well as for controlling the workflow inside the automated processing system.

The presently described method is based on the fact that it is so far only known in the art that loading slots of an automated processing system can only be used by particularly identifying the respective slot for loading a tray that carries sample tubes, or a loading slot for loading a tray that carries disposables/consumables like pipette tips. Accordingly, only the loading of samples and reagents in different randomized slots is well known, but not the combination of loading sample tubes containing a liquid and racks or carriers that only contain consumables/disposables like pipette tips in a simple way. Accordingly, the presently described inventive method offers a user-convenient way of loading samples and disposables into an automated processing system. The necessity of such improvement is based on the fact that the operator in a laboratory usually has to load a lot of different trays with supplies, consumables and samples into the loading slots of the automated processing system. Each of these trays has usually a different format and, thus, a different loading slot which is adapted to the format of the tray. However, with a multipurpose tray as described, each tray can have the same format for different samples and supplies. Accordingly, the operator can load the trays comprising supplies and/or samples into one or several random loading slots, without having to identify the matching loading slot each time a tray has to be loaded into the automated processing system.

As an example of the presently described inventive method, the automated processing system can be equipped with, e.g., 8 slots as tray interface between the outside and the inside of the automated processing system, wherein 4 of the slots can be assigned to be loading slots and the remaining 4 slots can be assigned to be unloading slots, for user convenience. For example, in an arrangement with two rows of slots, 4 slots on top arranged of the other 4 slots, the top 4 slots can be assigned to be the tray loading slots, and the bottom 4 slots can be assigned to be the tray unloading slots. Alternatively, all slots can be used for loading and unloading at the same time. Now, regarding the loading step of the presently described method, the multipurpose tray is loaded into any of the slots assigned to be a loading slot of the automated processing system, wherein the multipurpose tray can carry one or several universal tray inserts, one or several urine container tray inserts, and/or one or several tip rack tray inserts. Accordingly, as specific embodiment of the inventive method, the operator can fill sample or reagent tubes, or disposables, such as pipette tips, into the multipurpose tray as its content, wherein the step of loading the filled multipurpose tray into the loading slot or any loading slot of the automated processing system is carried out without the necessity of exchange of data regarding the format or content of the multipurpose tray with the software of the automated processing system. Due to the automatic recognition of the loaded tray by the automated processing system, the trays are loadable by the operator into the loading slots without the necessity of any user interaction with the software of the automated processing system, for example by means of a user interface or the like.

According to a further specific embodiment of the inventive method, the step of loading the multipurpose tray comprises loading a multipurpose tray with prioritized content into a predetermined loading slot of a plurality of loading slots, wherein the automated processing system carries out the processing step with prioritizing the multipurpose tray with prioritized content. Further, the predetermined loading slot can be a priority loading slot, and the prioritized content can be prioritized sample. For example, one of the 4 loading slots of the above described example can be designated to be the priority loading slot for prioritized trays, i.e. trays with prioritized content, such as prioritized samples that should be processed immediately, without getting in line behind other, non-prioritized samples. Thereby, the order of automated steps of processing sample can be influenced by the operator in this regard, if desired.

As further specific embodiment of the inventive method, the automated processing system can lock an unloading slot for preventing unloading of the multipurpose tray from the unloading slot before clearance, while the respective multipurpose tray is in processing. Accordingly, while each tray is in processing, the automated processing system prevents manual removal of the tray from the respective slot. Such prevention can be achieved by a manual lock or the like, holding the respective tray in the respective slot in place. Alternatively, or additionally, the automated processing system can comprise a loading/unloading status indicator for each slot, indicating the status of loading/unloading permission or loading/unloading prohibition for each slot. Thereby, in case the tray is not supposed to be unloaded, for example since processing of its content is still in process, the status indicator can signal the operator an unloading prohibition signal, for example in the form of a red light provided near the respective slot.

Regarding the unloading step of the present inventive method, it can be established that different kinds of tray with differing contents can be unloaded from the unloading slots. However, as a specific embodiment of the presently described method, one of the unloading slots can be designated to be an unloading slot for unloading sample error trays, i.e. trays with sample tubes that have been identified by the automated processing system to exhibit some kind of error, such as an unreadable label or the like, or also in case of an erroneous sample. Accordingly, the step of unloading the multipurpose tray can comprise unloading of a multipurpose tray with predetermined content from a predetermined unloading slot, wherein the predetermined content can be containers with erroneous samples.

The present invention is not limited to the particular methodology described herein because they may vary. Although any devices, methods and materials similar or equivalent to those described herein can be used in the practice of the present invention, the specific devices, specific methods and specific materials are described herein. Further, the terminology used herein is for the purpose of describing specific embodiments only and is not intended to limit the scope of the present invention.

In the context of the present invention, the term "automated processing system" as used herein refers to an automated laboratory system in a laboratory comprising one or more laboratory instrument(s) operatively connected to a control unit, such as an analytical, pre-analytical or post-analytical processing system, for automatically processing biological sample. In general, before a chemical, biological, physical, optical or other technical analysis can be performed on a sample by an analytical processing system, a variety of different pre-analytical processing steps may have to be executed on a sample of a patient by instruments of a pre-analytical processing system, such as sample centrifugation instrument for centrifuging a sample, sample resuspension instrument for resuspension of a sample, sample container capping or decapping instruments for capping and/or decapping a sample container, a recapping instrument for recapping a sample container after decapping the same, and/or aliquotation instrument for dividing a sample into aliquots of the sample, and the like. After the analysis, a variety of different pre-analytical processing steps may have to be executed on the sample by instruments of a post-analytical processing system, for example for executing one or more post-analytical processing steps on one or more biological samples, such as the verification and review of the analytical results, as well as the communication of these results to the operator of the laboratory system and their interpretation.

The term "laboratory instrument" or "instrument" of the laboratory as used herein encompasses any apparatus or apparatus component operable to execute one or more processing steps/workflow steps on one or more biological samples. The expression "processing steps" thereby refers to physically executed processing steps such as centrifugation, aliquotation, sample analysis and the like. The term "laboratory instrument" or "instrument" of the laboratory covers pre-analytical instruments, post-analytical instruments and also analytical instruments.

The term "pre-analytical" as used herein relates to the execution of one or more pre-analytical processing steps on one or more biological samples, thereby preparing the samples for one or more succeeding analytical tests. A pre-analytical processing step can be, for example, a centrifugation step, a capping-, decapping- or recapping step, an aliquotation step, a step of adding buffers to a sample and the like. The term "analytical" as used herein encompasses any process step carried out by one or more laboratory devices or operative units which are operable to execute an analytical test on one or more biological samples. The term "post-analytical" as used herein relates to the execution of one or more post-analytical processing steps on one or more biological samples, which steps begin with the verification and review of the analytical results, as well as to the communication of these results to the operator of the laboratory system and their interpretation.

The term "control unit" as used herein encompasses any physical or virtual processing device configurable to control a laboratory system comprising one or more laboratory instruments in a way that workflow(s) and workflow step(s) are conducted by the laboratory system. The control unit may, for example, carry different kinds of application software and instruct the laboratory system (or a specific instrument thereof) to conduct pre-analytical, post analytical and analytical workflow(s)/workflow step(s). The control unit may receive information from a data management unit regarding which steps need to be performed with a certain sample. Further, the control unit might be integral with a data management unit, may be comprised by a server computer and/or be part of one instrument or even distributed across multiple instruments of the laboratory system. The control unit may, for instance, be embodied as a programmable logic controller running a computer-readable program provided with instructions to perform operations.

The term "user interface" as used herein encompasses any suitable piece of application software and/or hardware for interactions between an operator and a machine, including but not limited to a graphical user interface for receiving as input a command from an operator and also to provide feedback and convey information thereto. Also, a system/device may expose several user interfaces to serve different kinds of users/operators.

In the context of biomedical research, analytical processing is a technical procedure to characterize the parameters of a biological sample or of an analyte. Such characterization of parameter comprises, for example, the determination of the concentration of particular proteins, metabolites, ions or molecules of various sizes in biological samples derived from humans or laboratory animals, or the like. The gathered information can be used to evaluate e.g. the impact of the administration of drugs on the organism or on particular tissues. Further analyses may determine optical, electrochemical or other parameters of the samples or the analytes comprised in a sample.

In the context of the present invention, an erroneous sample and/or an erroneous sample container will be determined as being not in the condition to be processed, i.e. not in the condition to be completed successfully, if an error occurred during the sample processing workflow and if the laboratory system was not able to continue the workflow run until its completion, which resulted in an undesired workflow run interruption.

The term "workflow" as used herein encompasses any task that comprises a number of steps, such as for maintenance or operation of the system or one of its system components.

The term "workflow step" as used herein encompasses any activity belonging to a workflow. The activity can be of an elementary or complex nature and is typically performed at or by one or more instrument(s).

The terms "sample" and "biological sample" refer to material(s) that may potentially contain an analyte of interest. The sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample can be suspected to contain a certain antigen or nucleic acid.

The term "sample tube" or "sample container" refers to any individual container for transporting, storing and/or processing a sample. In particular, the term without limitation refers to a piece of laboratory glass- or plastic-ware optionally comprising a cap on its upper end. Sample tubes, e.g. sample tubes used to collect blood, often comprise additional substances such as clot activators or anticoagulant substances which have an impact on the processing of the sample. As a consequence, different tube types typically are adapted for pre-analytical, analytical and/or post-analytical requirements of a particular analysis, e.g. a clinical chemistry analysis, a hematological analysis or a coagulation analysis. A mix-up of sample tube types can make (blood) samples unusable for analysis. To prevent errors in the collection and handling of samples, the sample caps of many tube manufacturers can be encoded according to a fixed and uniform color scheme. Some sample tubes types in addition or alternatively are characterized by particular tube dimensions, cap dimensions, and/or tube color. A dimension of a tube comprises e.g. its height, its size and/or further characteristic shape properties.

As used herein and in the appended claims, the singular forms "a", "an", and "the" include plural reference unless the context clearly dictates otherwise. Similarly, the words "comprise", "contain" and "encompass" are to be interpreted inclusively rather than exclusively; that is to say, in the sense of "including, but not limited to". Similarly, the word "or" is intended to include "and" unless the context clearly indicates otherwise. The terms "plurality", "multiple" or "multitude" refer to two or more, i.e. 2 or >2, with integer multiples, wherein the terms "single" or "sole" refer to one, i.e. =1. Furthermore, the term "at least one" is to be understood as one or more, i.e. 1 or >1, also with integer multiples. Accordingly, words using the singular or plural number also include the plural and singular number, respectively. Additionally, the words "herein," "above," and "below" and words of similar import, when used in this application, shall refer to this application as a whole and not to any particular portions of the application.

The description of specific embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize. Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The following examples are intended to illustrate various specific embodiments of the present invention. As such, the specific modifications as discussed hereinafter are not to be construed as limitations on the scope of the present invention. It will be apparent to the person skilled in the art that various equivalents, changes, and modifications may be made without departing from the scope of the present invention, and it is thus to be understood that such equivalent embodiments are to be included herein. Further aspects and advantages of the present invention will become apparent from the following description of particular embodiments illustrated in the figures.

LIST OF REFERENCE NUMERALS

Figure 1:
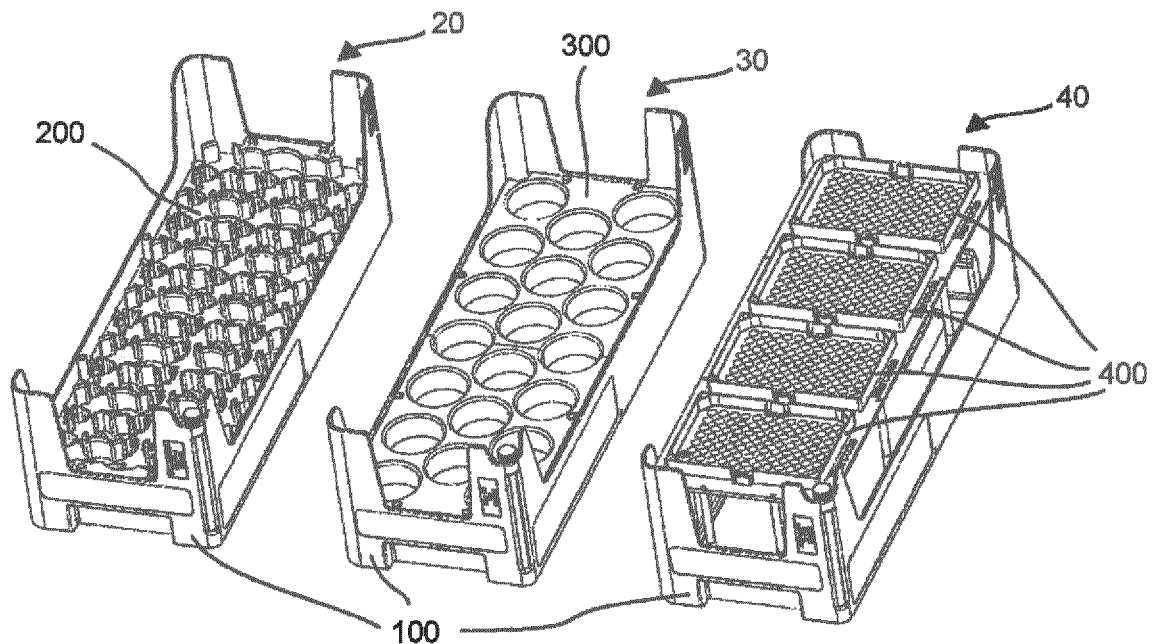
FIG. 1 is a schematic perspective illustration of several multipurpose trays according to an embodiment of the present invention, consisting of a base module and different tray inserts inserted therein, respectively, arranged next to each other for direct comparison.

10 loading/unloading station
11 flap door
12 loading slot
121 prioritized loading slot
13 unloading slot
131 error-out unloading slot
20 multipurpose tray for different sample tubes
20' alternative multipurpose tray for different sample tubes
30 multipurpose tray for urine sample containers
40 multipurpose tray for disposable pipette tips
100 base module
101 closed bottom
102 side plate
103 side slot/window
104 corner post
1041 corner post window
1042 top indentation
105 step portion
106 handle
1061 engagement indentation
107 color indicator
1071 rotary knob
108 writable surface
109 identification code
110 engagement protrusion
200 universal tray insert
201 large diameter tube receiving recess
201' large diameter tube receiving recess
2011 large diameter tube receiving recess center axis
202 middle diameter tube receiving recess
202' middle diameter tube receiving recess
2021 middle diameter tube receiving recess center axis
203 small diameter tube receiving recess
203' small diameter tube receiving recess
2031 small diameter tube receiving recess center axis
204 bracket
204' recess division bridge/bar
205' tube spring
210 engagement recess
220 fiducial markers
220' fiducial markers
230 color indicator groove
300 urine sample tray insert
301 urine sample container recess
400 tip rack tray insert
401 pipette tip hole
410 pipette tip rack
420 plug connector
501 large diameter sample tube
502 middle diameter sample tube
503 small diameter sample tube
601 urine sample container
701 pipette tip
800 centering spring
810 centering spring middle part
820 clamp arm
830 nib 831 pointed nib end
910 Decision step
920 Execution step
930 Execution step
940 Execution step
950 Execution step

DETAILED DESCRIPTION

Figure 2:
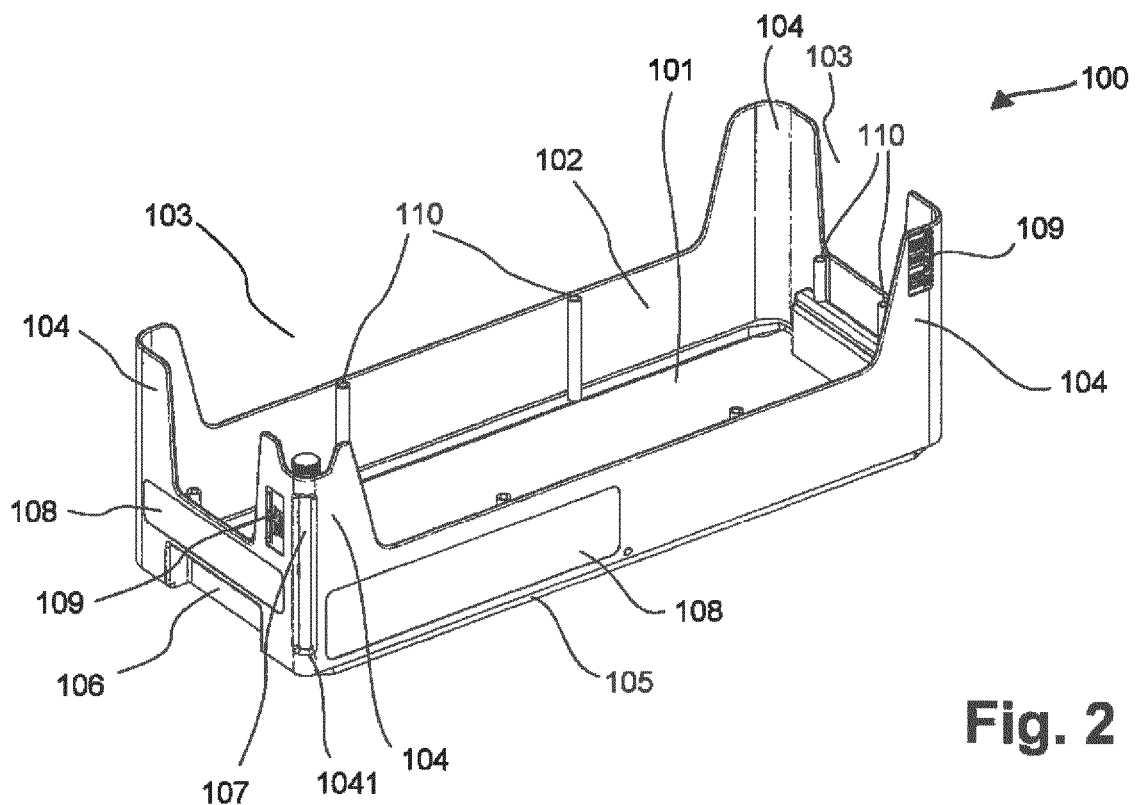
FIG. 2 is a schematic perspective illustration of a base module of any one of the multipurpose trays as shown in FIG. 1.

In FIG. 1, three different variations of a multipurpose tray according to an embodiment of the present invention are shown as schematic perspective illustrations arranged next to each other. According to the choice of tray insert, the purpose of the multipurpose tray can change. In particular, on the left side of FIG. 1, a multipurpose tray 20 with a base module 100 as shown in FIG. 2 and an empty universal tray insert 200 inserted therein is shown, without any sample tubes arranged in the universal tray insert 200. Further, in the middle position of FIG. 1, a multipurpose tray 30 with a base module 100 as shown in FIG. 2 and a urine sample tray insert 300 for urine sample containers inserted therein is shown, without any urine sample containers arranged in the urine sample tray insert 300. Moreover, on the right side of FIG. 1, a multipurpose tray 40 with a base module 100 as shown in FIG. 2 and a tip rack tray insert 400 with four tip racks inserted therein is shown, without any consumable pipette tips arranged in the tip rack tray insert 400. In the following, each of the multipurpose trays 20, 30, 40 and its particular structure is described in more detail based on respective illustrations in the drawings.

As general basis for each multipurpose tray 20, 30, 40, the base module 100 as shown in FIG. 2 is used, which base module 100 according to a specific embodiment of the present invention basically consists of one integrally formed component, which can be injection-molded from polypropylene (PP) or a polycarbonate blend, such as polycarbonate with styrene acrylonitrile (PC/SAN) or polycarbonate with acrylonitrile-butadiene-styrene (PC/ABS). The base module 100 of the presently described specific embodiment is a general box-like structure with a closed bottom 101, a circumferentially extending side plate 102 in the form of four thin-walled side walls connected with each other and connected with the bottom 101, and an open upper side. Inside the base module 100, protrusions 110 are provided on the inner wall surface of the side plate 102, which protrusions 110 are cylindrically formed columns with a center hole, respectively, which annular columns are protruding laterally inward from the side plate 102, i.e. the protrusions 110 are connected, at their base end, with the closed bottom 101, and each protrusion 110 is integrally connected with the side plate 102 by means of an integrally formed connection part. Here, in the presently described specific embodiment, 8 protrusions 110 are provided.

Figure 5:
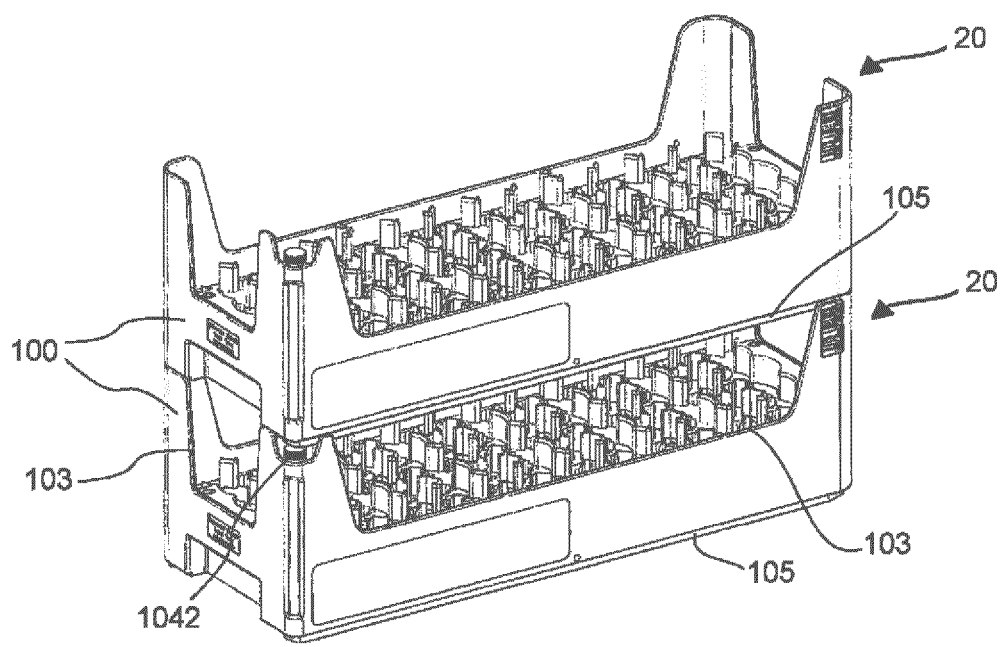
FIG. 5 is a schematic perspective illustration of two multipurpose trays, each with a base module as shown in FIG. 1 and an empty universal tray insert inserted therein, stacked on top of each other.
Figure 19:
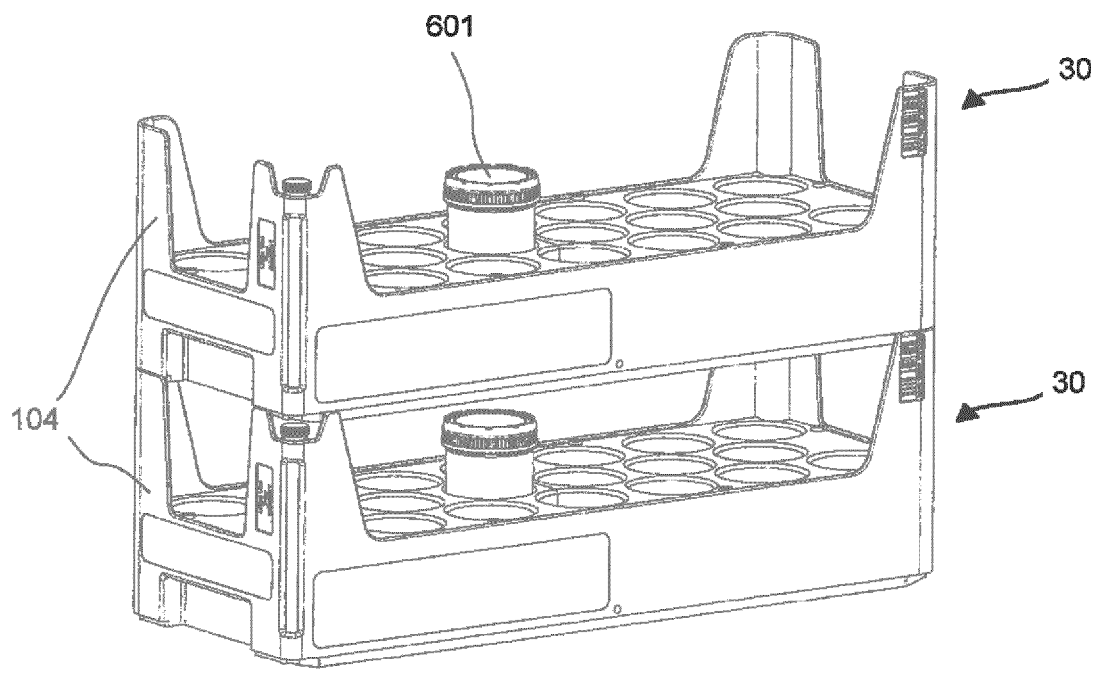
FIG. 19 is a schematic perspective illustration of two multipurpose trays as shown in FIG. 18, stacked on top of each other, each with one single urine sample container provided therein.

Each protrusion 110 constitutes an engagement protrusion 110 for engagement with a respective engagement feature of one of the tray inserts 200, 300, 400, which will be described later in more detail. In each side wall of the side plate 102, an open side slot 103 is provided, which side slot 103 extends from the open upper side, i.e. the open upper side continues in the open side slot 103, thereby constituting four windows of the side plate 102 open to the top. Here, the protrusions 110 only extend over the extent of the respective side wall, i.e. the protrusions 110 do not extend upwards into the open side slot 103. As a result of the provided side slots 103, each corner of the rectangular base module 100 constitutes an angular corner post 104 starting from the closed bottom 101 and continuing to the open upper side, which angular corner posts 104 generate sufficient distance between the closed bottom 101 and the open upper side for the base module 100 to be able to receive at least one of the tray inserts 200, 300, 400 as well as the respective content provided therein, without interacting with another base module 100 stacked on top of it, as is illustrated, for example, in FIGS. 5 and 19. Accordingly, the base module 100 is stackable on top of another base module 100 of the same type, resulting in a stackability of the base modules 100 in a space saving manner, independent from the tray insert 200, 300, 400 provided in each of the stacked base modules 100. In order to achieve the stacking connection between at least two base modules 100 on top of each other, the bottom side of the bottom 101 of each base module 100 comprises a step portion 105 with reduced outer circumference, i.e. the step portion 105 is formed as a narrowing step portion, which step portion 105 matches into an inner side of an upper edge of the open side of another base module 100, or more specifically into the inner side of the thin-walled angular corner posts 104 of such base module 100. Accordingly, the step portion 105 on the bottom 101 of the upper base module 100 can be stacked into an upper edge of the open side of another base module 100, e.g. in a nestable manner, see FIGS. 5 and 19. As can also be gathered from FIGS. 5 and 19, besides a weight reduction of the base module 100, the side slots 103 in the side plate 102 of each base module 100 also result in an improved visibility of the content of the respective tray insert 200, 300, 400 from the outside, which further improves the handling, such as transport or the like, of the multipurpose trays 20, 30, 40.

Furthermore, as shown in most of the drawings, such as in, for example, FIGS. 1 to 5, the base module 100 comprises two handles 106 on its outer circumference, i.e. on the outer side of the side plate 102, for improved transportability of the base module 100 by an operator, wherein the handles 106 are provided in opposite side walls, thus opposite to each other, and wherein each handle 106 simplifies a grasping of the base module 100 by the operator. The handles 106 are provided in an integral manner inside the side plate 102, i.e. formed in the manner of side pockets protruding into the inside of the base module 100, as can be gathered from FIG. 2. Here, it is to be noted that the handles 106 do not interfere with the step portion 105 and, thus, do not interfere with the stackability feature of the base module 100. Furthermore, since the open side of the handle 106, i.e. the open side of the pocket formed by the handle 106 is open to the side, an operator is able to grasp into the respective handle 106 even when the base module 100 is stacked on top of another base module 100, see also FIGS. 5 and 19.

Figure 3:
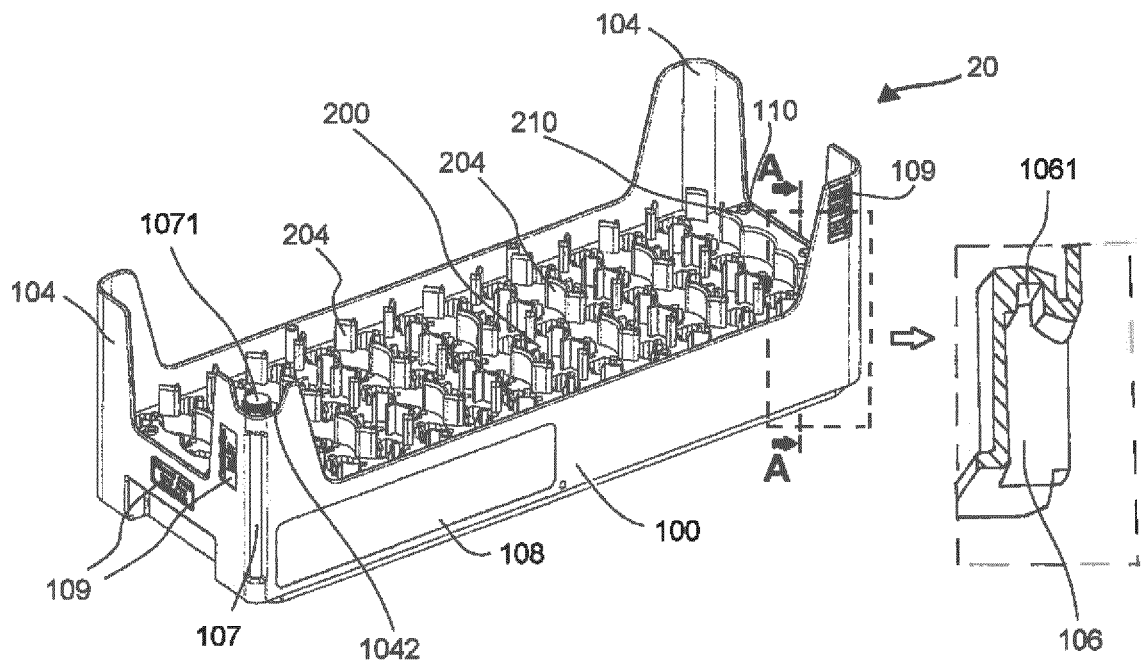
FIGS. 3 and 4 are schematic perspective illustrations of a multipurpose tray with a base module as shown in FIG. 1 and an empty universal tray insert inserted therein, viewed from different angles, as also shown in FIG. 1 on the left side, wherein FIG. 3 comprises an enlarged detail of the inner structure of a handle of the base module in a longitudinal cross section along line A-A.

Moreover, the base module 100 of the presently described specific embodiment can comprise, as a further interface, an engagement indentation 1061 on its outer circumference, as can be gathered from the enlarged detail illustration in FIG. 3 in a partial cross sectional view along line A-A. Here, the engagement indentation 1061 is not to be confused by one of the handles 105 itself as described above, but is particularly provided inside the inner structure of the respective handle 105 for a tray carrier, or tray carrier instrument such as a tray shuttle or the like, of the automated processing system, for improved transportability of the base module 100 by the tray carrier in the course of an automated transportation process. In more detail, one or more engagement indentations 1061 are provided within each handle 105, wherein each engagement indentation 1061 is formed in the shape of a notch provided inside a handle pocket of each handle 105.

As further feature of the base module 100 as depicted in FIG. 2, the base module 100 comprises a rotatable color indicator 107 for indication of a loading status of a content of a multipurpose tray 20, 30, 40, i.e. a content of a tray insert 200, 300, 400 as received in the base module 100 of the multipurpose tray 20, 30, 40. Here, the color indicator 107 is provided in the form of a manually operable rotating indicator pin or pole arranged in a respective stud hole provided in one of the corner posts 104 of the base module 100, wherein the stud hole comprises a viewing window 1041 to the outside of the base module 100, in which the respective color can be shown and changed by rotation of the color indicator 107. The color indicator 107 in the form of the described pin embedded in the hole in the respective corner post 104 comprises an actuation portion in the form of a rotary knob 1071, see also FIG. 3. The respective corner post 104 comprising the stud hole for the indicator post 107 exhibits a top indentation 1042 at its top end, in which the rotary knob 1071 is arranged in a rotatable manner, so that the rotary knob 1071 does not extend over the upper edge of the corner post 104, in order to maintain the stackability property of the base module 100, see FIG. 5. Due to the color indicator 107, its stud hole and the top indentation 1042 at its top end, the loading direction of the base module 100 can clearly be determined, since, referring to its geometry, a tray comprising the base module 100 can also be loaded into loading slots of an automated processing system with a turn of 180° around its Z-pivot, i.e. with the color indicator 107 on its back end, since the structural marks in the form of the color indicator 107, its stud hole and the top indentation 1042 at its top end are detectable by optical sensors of the automated processing system, enabling the same to detect if the tray was wrongly provided into one of the loading slots. Here, following states can be detected: "Tray not available", "Tray available", and "Tray available (inverted loading with a turn of 180°)"

As one particular color example, the color indicator 107 can provide four different colors, which can indicate that the multipurpose tray 20, 30 has new, i.e. unprocessed, content, already processed content, content designated for the archive, or erroneous content, wherein the unprocessed content can be color-coded with green color and the already processed content, or alternatively erroneous content, can be color-coded with red color. Also, in case that the multipurpose tray 40 carries content that is not in need of loading status indication, for example in case the tray insert 400 carries consumable tips or the like, i.e. content without any status, a so-called blind plug can be fitted into the stud hole of the corner post 104 instead of the color indicator 107, i.e. a plug without any different colors provided on it, such as a grey-colored plug or the like. Accordingly, the color indicator can be replaced, if desired, for improved user convenience. The color indicator 107 as described above is particularly useful when using the universal tray insert 200 which can hold different kinds of sample tubes, or when using a urine sample container tray 300. On the other hand, a blind plug can be reasonable when using a consumable tips carrying tray insert 400, as mentioned before. Here, such blind plug can have the same structural design as the color indicator 107, however without any color markings on its outer circumference.

According to a further aspect of the presently discussed specific embodiment of the inventive base module 100, the base module 100 can comprise two writable surfaces 108 on the outer circumference of the side plate 102, in order for an operator to provide the base module 100 with a human readable marking and allowing rapid marking and erasing of such markings on the surface of the base module 100 by a human operator, if desired, wherein each writable surface 108 is implemented by means of a whiteboard material, i.e. a wipeable material. Moreover, the base module 100 can have one or several identification codes 109 on its outer circumference, which can be an adhesive label or the like, carrying a human-readable machine-writing or a machine-readable identification code 109 implemented by a barcode, both of which are provided on the side plate 102 of the base module 100 as illustrated in FIG. 2.

In FIG. 3, a multipurpose tray 20 is shown, similar to the illustration on the left side of FIG. 1, comprising the above described base module 100, with an empty universal tray insert 200 inserted therein, without any sample tubes arranged in the universal tray insert 200. Here, it is to be noted that the universal tray insert 200 can be provided in one single piece inserted into the base module 100, but the universal tray insert 200 can also be provided in the form of two or more pieces, for easier insertion. Furthermore, in this specific embodiment of a multipurpose tray 20, however, only one writable surface 108 but two identification codes 109 carrying a human-readable machine-writing and one machine-readable identification code 109 are provided on the outer circumference of the side plate 102. The remaining features of the base module 100 are identical to the above described base module 100, i.e. the basic structure of the base module 100 is maintained, wherein the application of external features, i.e. the application of writable surfaces 108 or identification codes 109 on the outside of the base module 100, slightly varies.

Figure 4:
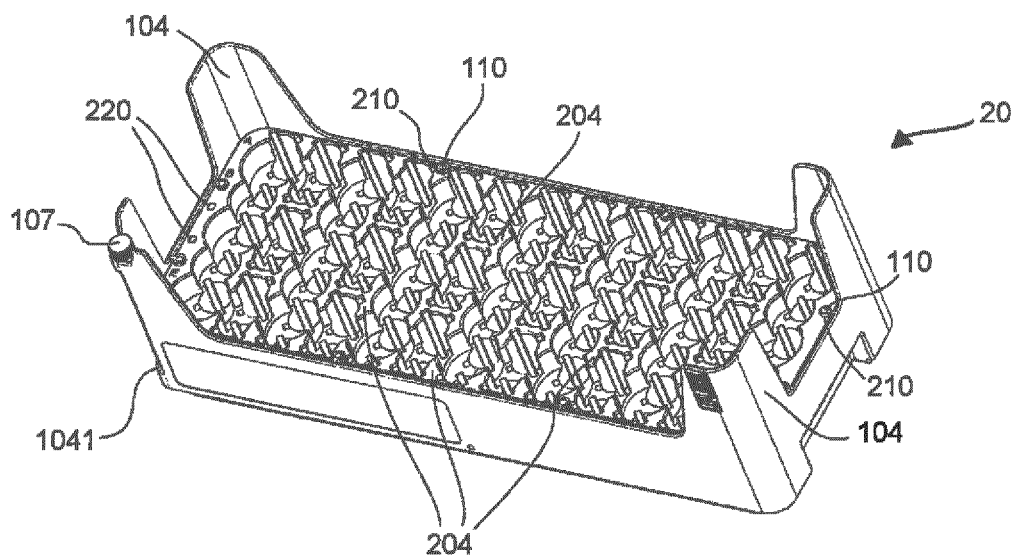

As can be gathered from FIGS. 3 and 4, the universal tray insert 200 comprises 8 circular engagement recesses 210 on its outer edge, which engagement recesses 210 establish a form-fit connection in the form of a releasable push-in connection with the protrusions 110 of the base module 100, i.e. the protrusions 110 of the base module 100 provide a tongue of a tongue-and-groove connection, wherein the engagement recesses 210 of the tray insert 200 provide the groove counterpart. Also, the circumferential edge of the entire universal tray insert 200 matches the inner circumference of the side plate 102 of the base module 100, which supports the releasable push-in connection between base module 100 and universal tray insert 200. Furthermore, as can be gathered particularly from FIG. 4 which shows the multipurpose tray 20 of FIG. 3 from a different viewing angle, fiducial markers 220 are provided at the edge of an upper surface of the universal tray insert 200, which fiducial markers 220 are used for clear allocation of each of the tube receiving recesses in the universal tray insert 200 and can be provided in the form of a grid consisting of alphabetic characters and/or numbers, for identifying each tube receiving recess in the universal tray insert 200. Here, in the embodiment as depicted in FIG. 4, the fiducial markers 220 designating the rows of tube receiving recesses are shown in capital letters. However, as an alternative, the fiducial markers 220 could also be provided on the outer circumference of the side plate 102 of the base module 100, for example by printing or by means of additional adhesive labels.

Figure 6:
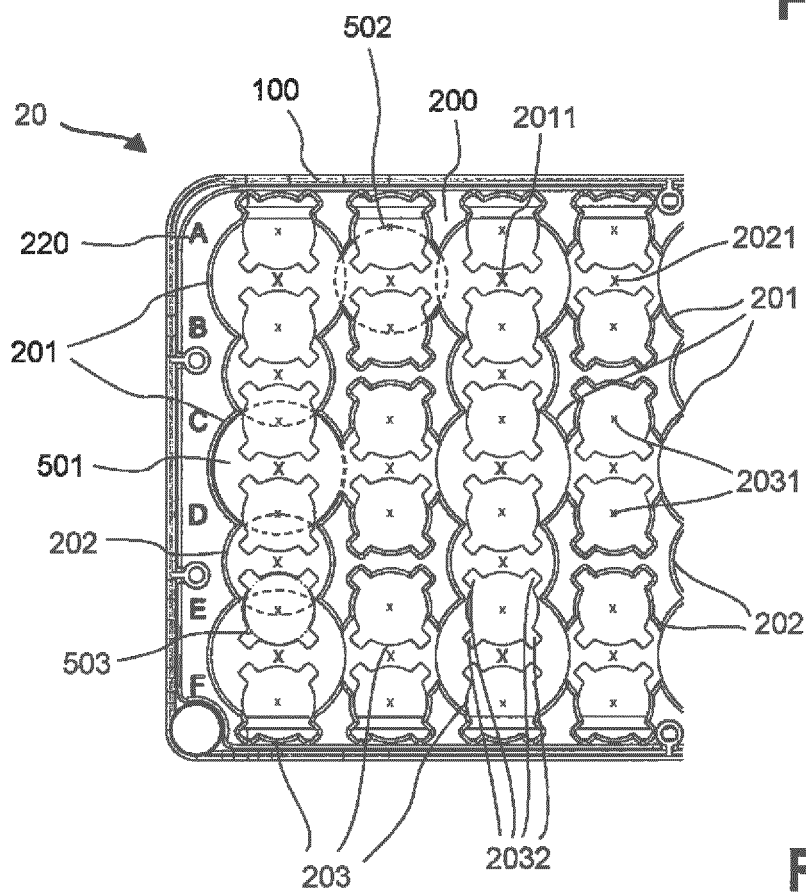
FIG. 6 is an enlarged detail of a top view of a left side of the multipurpose tray as shown in FIGS. 3 and 4.
Figure 7:
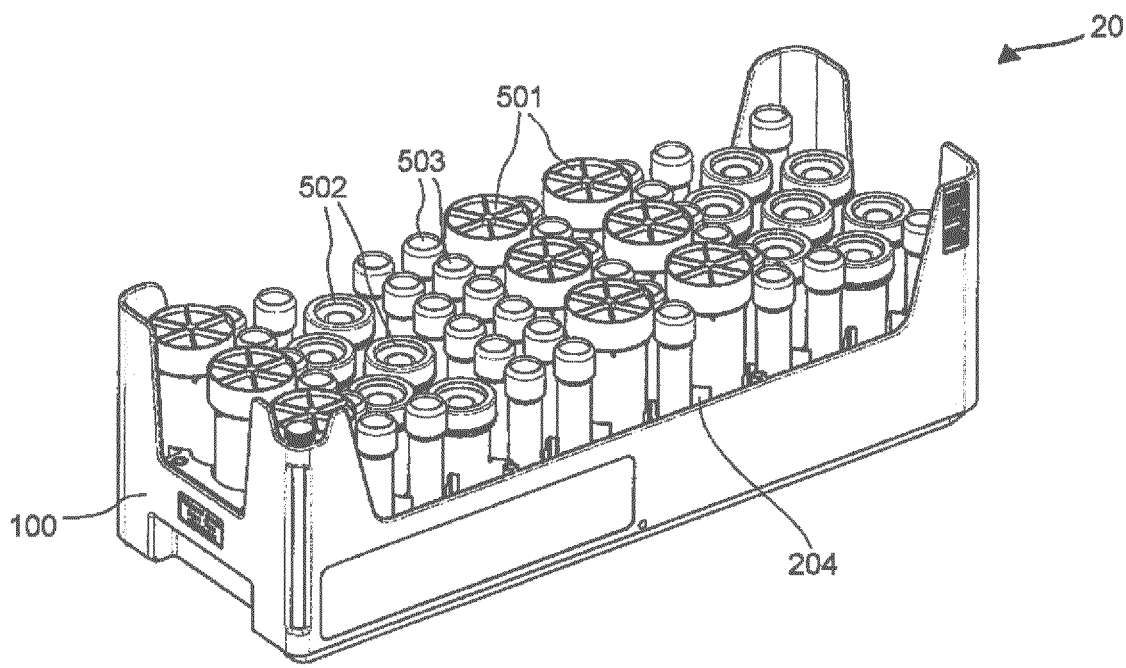
FIG. 7 is a schematic perspective illustration of a multipurpose tray with a universal tray insert inserted therein, and with different kinds of containers mixedly arranged therein next to each other in an optimized manner.
Figure 8:
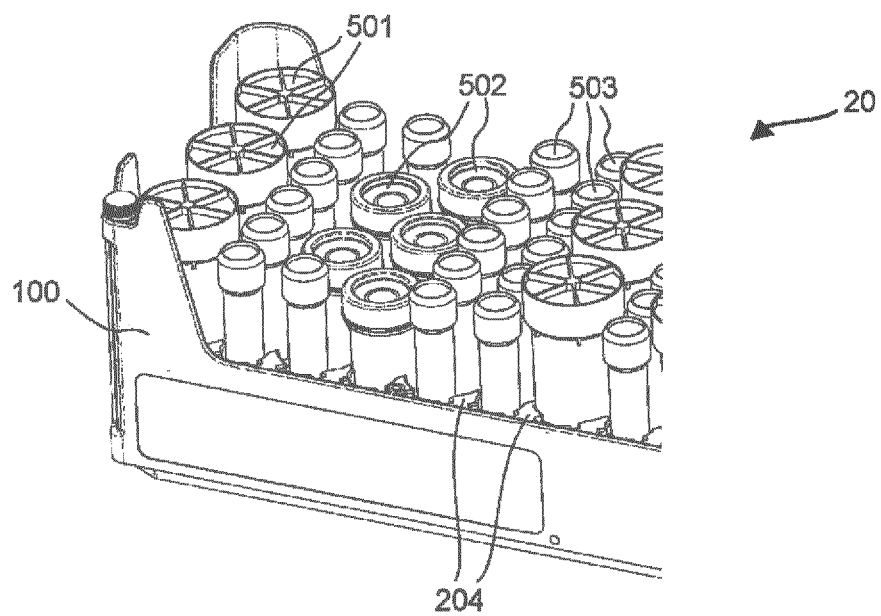
FIG. 8 is an enlarged detail view of the left side of the multipurpose tray as shown in FIG. 7.
Figure 9:
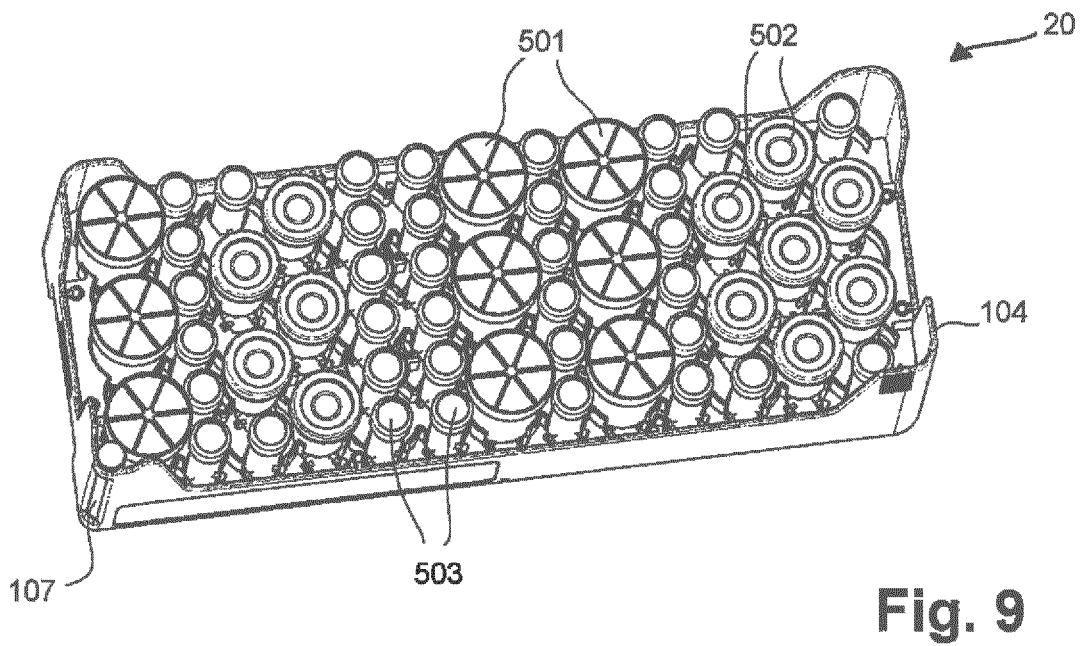
FIG. 9 is a schematic perspective illustration of the multipurpose tray as shown in FIG. 7, viewed from a different angle.
Figure 10:
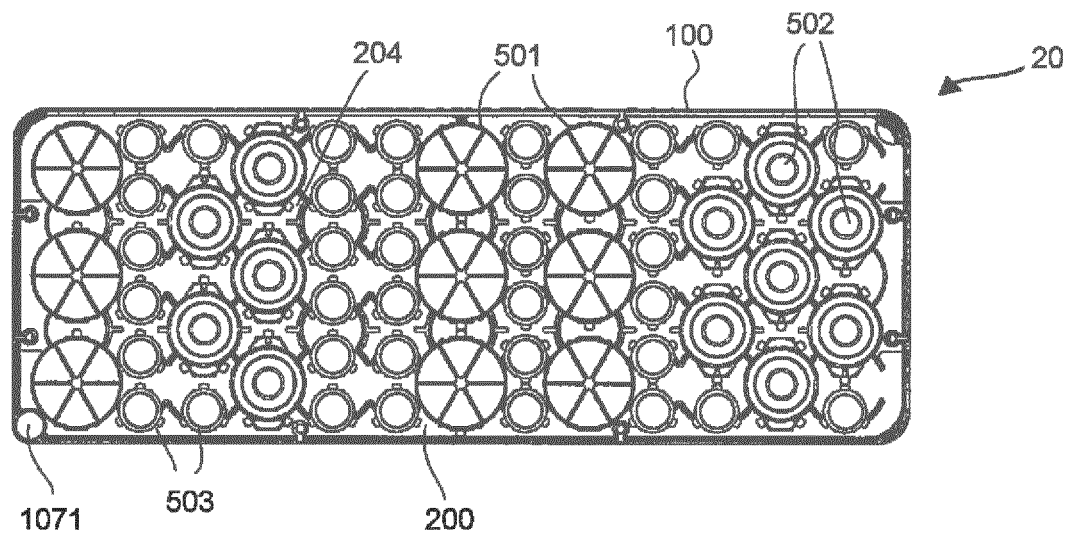
FIG. 10 is a top view of the multipurpose tray as shown in FIGS. 7 to 9.

Regarding the structure of tube receiving recesses in the universal tray insert 200 of the presently described specific embodiment, there are several different kinds of tube receiving recesses provided as a tube receiving recess array in the universal tray insert 200 as shown in FIGS. 1 and 3 to 5, which can clearly be derived from the detail of a top view of a left side of the multipurpose tray 20 as shown in FIG. 6. Here, the array of tube receiving recesses comprises a first group of tube receiving recesses 201 with a large diameter, in order to receive sample tubes with a large outer diameter, such as PreservCyt tubes, a second group of tube receiving recesses 202 with a middle sized diameter, i.e. a smaller diameter compared to the tube receiving recesses 201, in order to receive sample tubes with a middle sized outer diameter, such as SurePath tubes, and a third group of tube receiving recesses 203 with a small diameter, i.e. an even smaller diameter compared to the other tube receiving recesses 201, 202, in order to receive sample tubes with a small outer diameter, such as PCR tubes. For clarification, in the enlarged detail of the universal tray insert 200 as shown in FIG. 6, 6 full, i.e. uncropped, tube receiving recesses 201 of the first group, 10 full tube receiving recesses 202 of the second group, and 24 full tube receiving recesses 203 of the third group are shown. Moreover, for illustrative reasons only, one exemplary sample tube 501 with a large outer diameter is shown in one of the tube receiving recesses 201 of the first group in the left column in the middle position, depicted by means of a dashed circular line and arranged next to the capital letters "C" and "D" of the fiducial markers 220, one exemplary sample tube 502 with a middle sized diameter is shown in one of the tube receiving recesses 202 of the second group in the second to left column in the uppermost position, depicted by means of a dashed circular line, and one exemplary sample tube 503 with a small diameter is shown in one of the tube receiving recesses 203 of the third group in the left column in the second position counted from the lower side of the illustration, depicted by means of a dashed circular line and arranged next to the capital letter "E" of the fiducial markers 220. Here, in order to depict the correlation between the diameters of the exemplary sample tubes 501, 502, 503 and the intersecting tube receiving recesses 201, 202, 203, the intersecting parts of the same are also depicted in a dashed circular manner, for the sake of improved perceptibility. Here, as an optional feature, the inner diameter of each tube receiving recess 201, 202, 203 can provide lash/tolerance to some extent, so that a respective sample tube 501, 502, 503 provided with one or several labels on its outer circumference can still fit into the respective tube receiving recess 201, 202, 203.

As described above, the size of a tube receiving recess 201 of the first group, the size of a tube receiving recess 202 of the second group and the size of a tube receiving recess 203 of the third group differ from each other, i.e. the recess sizes between those groups are different to each other. Moreover, a contour of an inner circumference of each tube receiving recess 201 of the first group, which basically coincides with the dashed circular line of the large diameter sample tube 501, intersects with a contour of an inner circumference of at least one adjacent tube receiving recess 202 of the second group, which basically coincides with the dashed circular line of the middle diameter sample tube 502. Here, as contour of a tube receiving recess inner circumference, an outline of the tube receiving recess inner circumference is to be understood, wherein the contour or outline of the tube receiving recess inner circumference also be identified as the substantial cross-section of the respective tube receiving recess when viewed from above, as in FIG. 6. However, as can also be gathered from FIG. 6, the inner circumferences of the tube receiving recesses 201, 202 of both the first group and the second group are not continuous, since the tube receiving recesses 201, 202 of both groups intersect with each other, thus exhibiting an intersection of the contour of a tube receiving recess inner circumference of the first group of tube receiving recesses 201 with the contour of an inner circumference of at least one adjacent tube receiving recess 202 of the second group of tube receiving recesses 202. Also, the intersection of contours of the first group of tube receiving recesses 201 and the second group of tube receiving recesses 202 constitutes a non-tangential crossover of contours, meaning that the contour of an inner circumference of each tube receiving recess 201 of the first group crosses the contour of an inner circumference of at least one adjacent tube receiving recess 202 of the second group in a non-tangential manner. Such arrangement of tube receiving recesses 201, 202 specifically assists in achieving the optimized way of fitting tubes with two differing diameters into the universal tray insert 200, in order to achieve an increase in receivable tube number that can be inserted into the universal tray insert 200.

Furthermore, it is to be noted that a center axis 2011 of each respective tube receiving recess 201 of the first group is arranged in an eccentric manner in relation to a center axis 2021 of an adjacent tube receiving recess 202 of the second group, meaning that the center axes 2011, 2021 of both groups of tube receiving recesses 201, 202 do not coincide with each other, which additionally assists in achieving the already described optimized way of fitting tubes with differing diameters into the universal tray insert 200. Here, the distances between the respective axes 2011, 2021 are set in a way in accordance with the respective sample tubes 501, 502 to be loaded so that a "wrong" loading of the sample tubes 501, 502 into the universal tray insert 200 is not possible, or at least can easily be detected by the operator during loading. Moreover, a depth of each tube receiving recess 201 of the first group can be different from a depth of each tube receiving recess 202 of the second group, depending on the length of the respective sample tubes 501, 502 to be inserted therein. Thereby, sample tubes 501, 502 with differing length can also be received by the universal tray insert 200, wherein the depth of the different groups of tube receiving recesses 201, 202 can be chosen such that the tops of sample tubes having a longer length do not or only slightly protrude compared to the other group of tubes having a shorter length.

As already described above, the tube receiving recess array of the universal tray insert 200 of the multipurpose tray 20 comprises the tube receiving recesses 203 of the third group, additionally to the already described first and second groups of tube receiving recesses 201, 202, wherein a contour of an inner circumference of at least one of tube receiving recesses 203 of the third group, which basically coincides with the dashed circular line of the small diameter sample tube 503, intersects with a contour of an inner circumference of at least one adjacent tube receiving recess 201, 202 of the first and/or second group. Here again, as contour of an inner circumference of a tube receiving recess 203, an outline of the inner circumference of the tube receiving recess 203 is to be understood, wherein the contour or outline of the inner circumference of the tube receiving recess 203 can also be identified as the substantial cross-section of the tube receiving recess 203 when viewed from above. Also, a center axis 2031 of each respective tube receiving recess 203 of the third group is arranged in an eccentric manner in relation to the center axis 2011 of an adjacent tube receiving recess 201 of the first group and to the center axis 2021 of an adjacent tube receiving recess 202 of the second group, meaning that the center axes 2011, 2021, 2031 of all groups of tube receiving recesses 201, 202, 203 do not coincide with each other. However, regarding the contour of the tube receiving recesses 203, it has to be noted that, different from the contours of the tube receiving recesses 201, 202, each contour of the tube receiving recesses 203 comprises 4 axial slots 2032 provided in a manner of always two slots 2032 being arranged opposite of each other, i.e. resulting in a general X-shape of the axial slots 2032. The axial slots 2032 are provided for manufacturing reasons.

In addition to the respective observations above regarding the first and second groups of tube receiving recesses 201, 202, the inner circumferences of the tube receiving recesses 201, 202, 203 of all three groups of the presently described specific embodiment are not continuous, wherein the tube receiving recesses 201, 202, 203 of all groups can intersect with each other when viewed from above, thus exhibiting an intersection of the contour of an inner circumference of each tube receiving recess 201 of the first group with the contour of an inner circumference of at least one adjacent tube receiving recess 202 of the second group and also with the contour of an inner circumference of at least one adjacent tube receiving recess 203 of the third group. This additionally assists in achieving the already described optimized way of fitting tubes with differing diameters into the universal tray insert 200. Further, the distances between the respective axes 2011, 2021, 2031 are set in a way in accordance with the respective sample tubes 501, 502, 503 to be loaded so that a "wrong" loading of the sample tubes 501, 502, 503 into the universal tray insert 200 is not possible, or at least can easily be detected by the operator during loading. With such a particular structure of tube receiving recesses 201, 202, 203 with differing sizes, the design of the universal tray insert 200 can be further improved in that it can receive three different container shapes or sizes of the sample tubes 201, 202, 203, wherein it again becomes possible to merge smaller containers closer together than bigger containers. Accordingly, the three differing types of sample tubes 501, 502, 503 with three differing diameters can fit in the universal tray insert and, thus, in the respective multipurpose tray, always in an optimized way, in order to achieve an increase in receivable tube number that can be inserted into the universal tray insert 200. For example, in case only one of the three different sample tube types is loaded into the universal tray insert 200 of the presently described design, it becomes possible to load 21 pieces of sample tubes 501 with large diameter, such as PreservCyt tubes, 32 pieces of sample tubes 502 with a middle sized diameter, such as SurePath tubes, or 78 pieces of sample tubes 503 with a small diameter, such as PCR tubes. Thus, the universal tray insert 200 of the presently described specific embodiment can receive between 21 and 78 sample tubes, of the same type or of different types in a mixed manner, depending on the composition of loaded sample tubes 501, 502, 503.

Regarding the depth of the tube receiving recesses 203 of the third group, it has to be noted that the same are partially provided in the bottom of one or several of the tube receiving recesses 201, 202 of the first and second group, meaning that the depth of the tube receiving recess 203 of the third group is deeper than the depth of the tube receiving recesses 201, 202 of the first and second group. This can also be gathered from FIGS. 3 and 4. Based on the different depths, the different sizes and the eccentric arrangement of the tube receiving recesses 201, 202, 203 of all groups, the universal tray insert 200 comprises brackets 204 protruding from a bottom of the universal tray insert 200 and surrounding the tube receiving recesses 201, 202, 203, which brackets 204—when fully shaped, i.e. not provided at the edge of the universal tray insert 200 but rather to the middle-exhibit a substantial shape in the form of the capital letter "H".

With the above described structure of the universal tray insert 200, different types of sample tubes 501, 502, 503 with differing diameters can fit in the universal tray insert 200 and, thus, in the respective multipurpose tray 20, always in an optimized way, in order to achieve an increase in receivable tube number that can be inserted into the universal tray insert 200, see also FIGS. 7 to 10. Here, as an example as depicted in FIGS. 7 to 10, 6 large diameter sample tubes 501, such as PreservCyt tubes, 12 middle diameter sample tubes 502, such as SurePath tubes, and 36 small diameter sample tubes 503, such as PCR tubes, are loaded into the universal tray insert 200 of the multipurpose tray 20, in a mixed manner.

Figure 11:
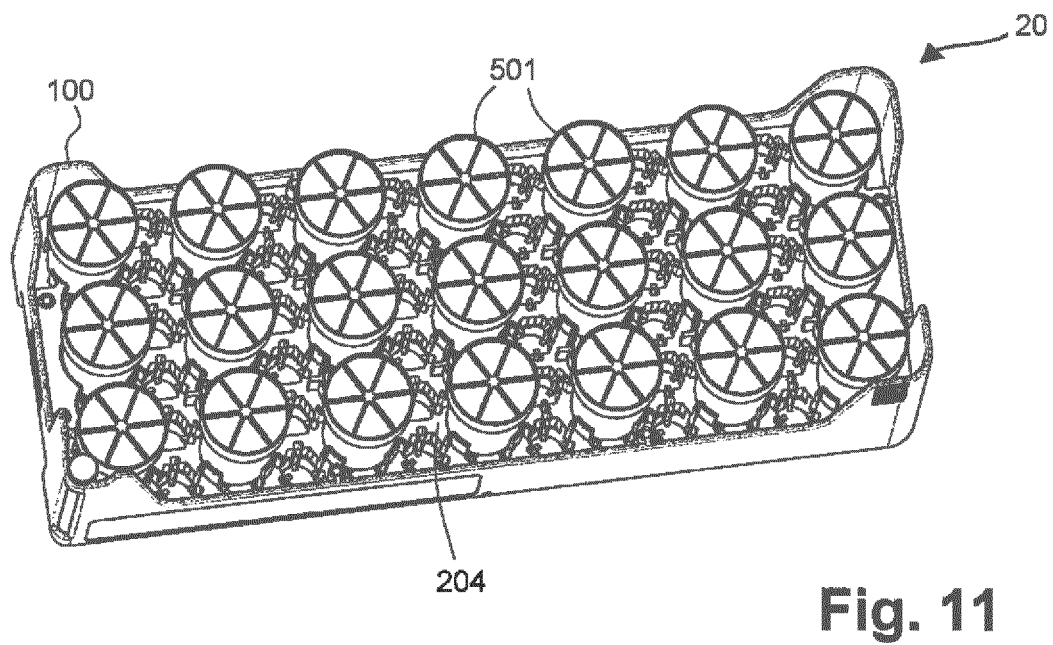
FIG. 11 is a schematic perspective illustration of a multipurpose tray with a universal tray insert inserted therein, fully filled with containers of one and the same kind, comprising a large diameter, and arranged therein next to each other in an optimized manner.
Figure 12:
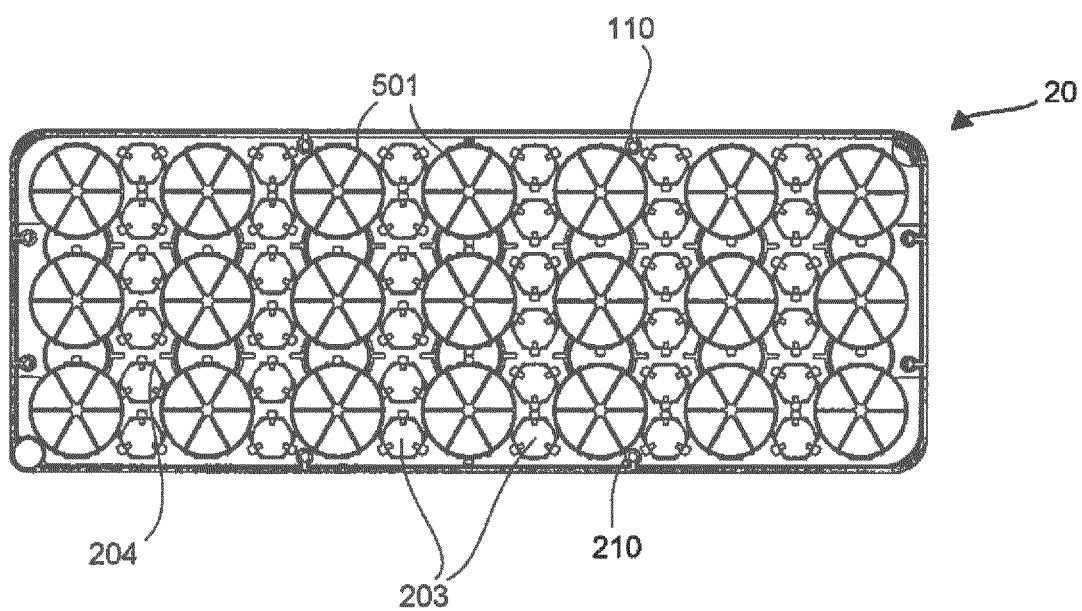
FIG. 12 is a top view of the multipurpose tray as shown in FIG. 11.
Figure 13:
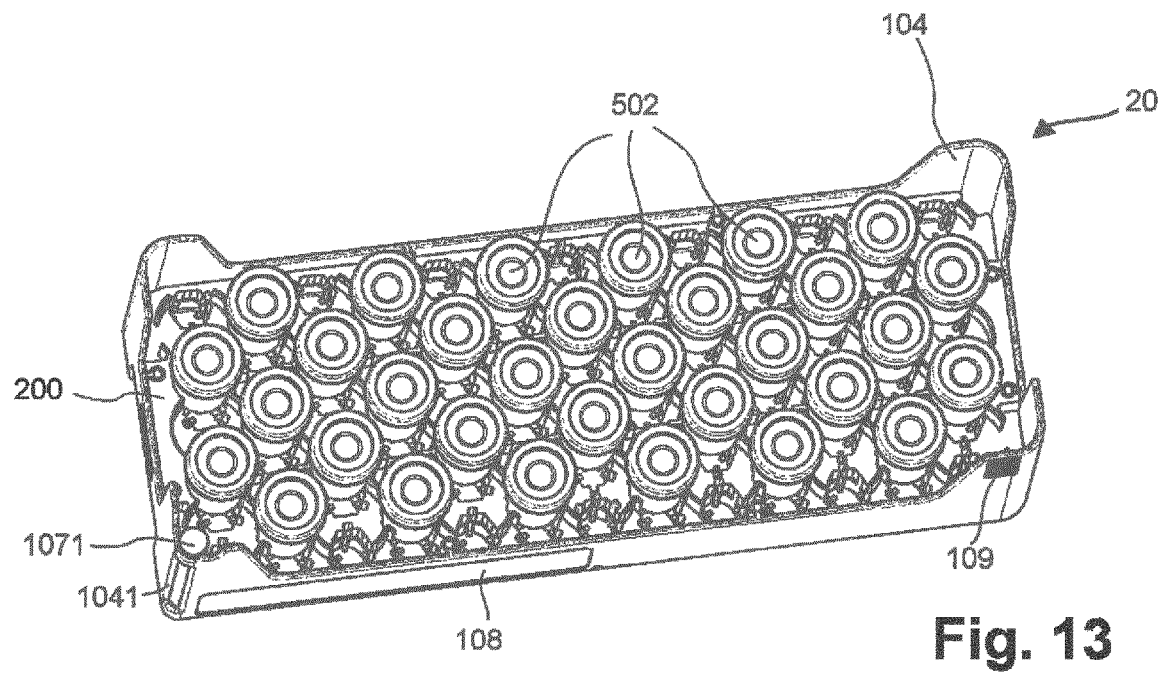
FIG. 13 is a schematic perspective illustration of a multipurpose tray with a universal tray insert inserted therein, fully filled with containers of one and the same kind, comprising a mid-sized diameter, and arranged therein next to each other in an optimized manner.
Figure 14:
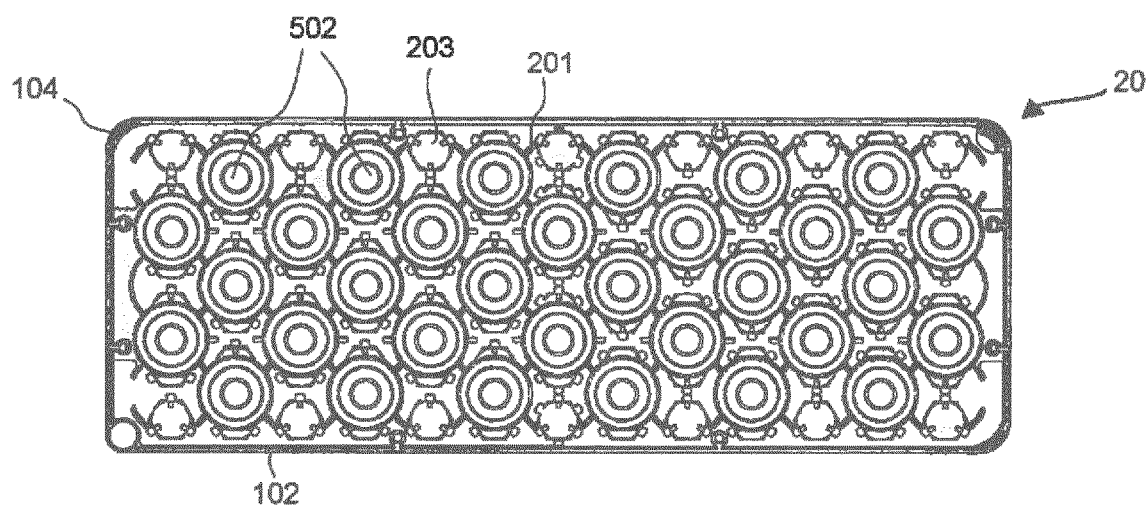
FIG. 14 is a top view of the multipurpose tray as shown in FIG. 13.
Figure 15:
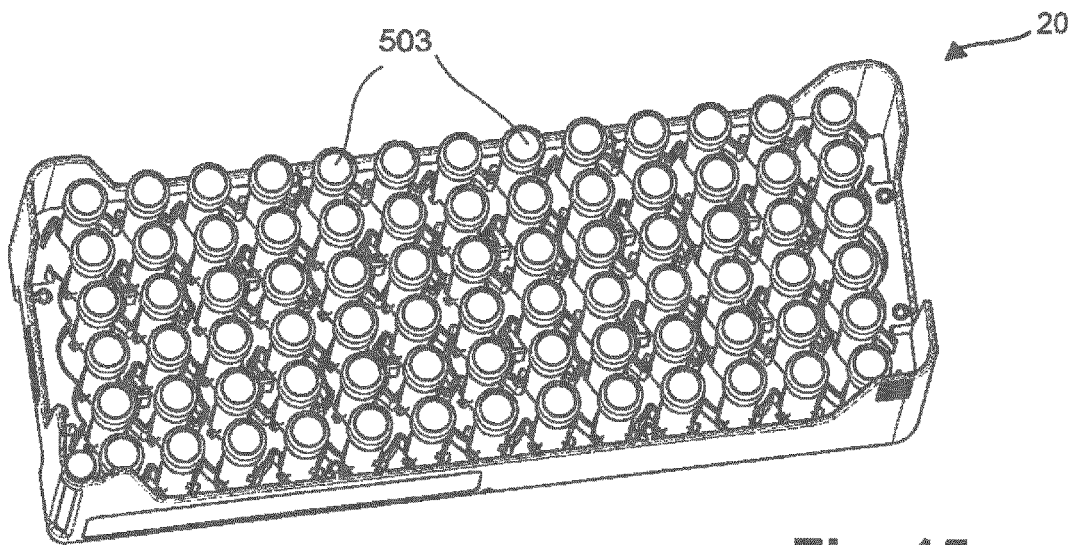
FIG. 15 is a schematic perspective illustration of a multipurpose tray with a universal tray insert inserted therein, fully filled with containers of one and the same kind, comprising a small diameter, and arranged therein next to each other in an optimized manner.
Figure 16:
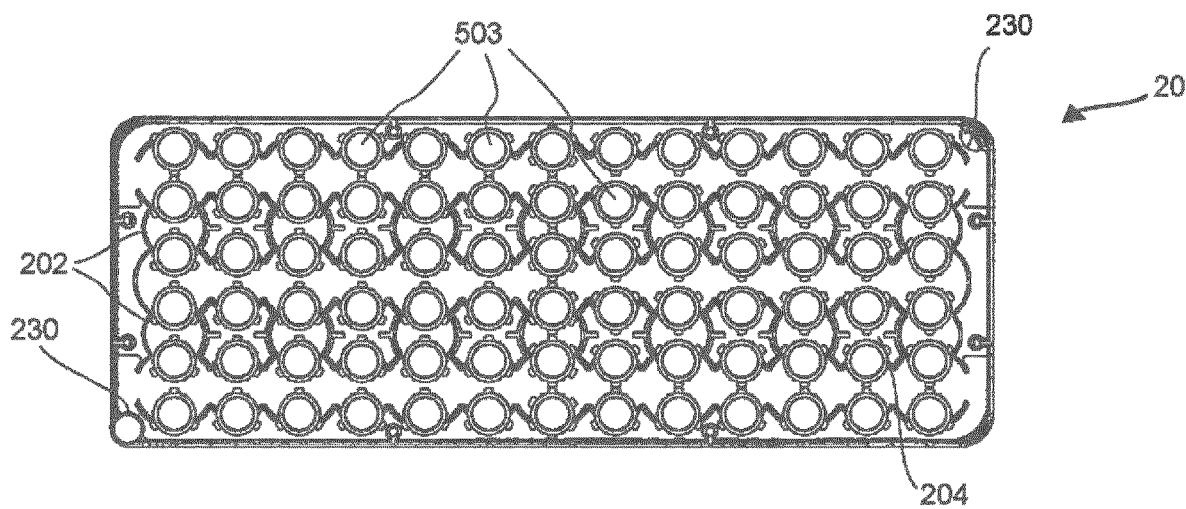
FIG. 16 is a top view of the multipurpose tray as shown in FIG. 15.

However, the universal tray insert 200 can also only be filed with one single type of sample container. Here, with the above described structure of the universal tray insert 200 of the presently described embodiment of the multipurpose tray 20 and as shown in FIGS. 11 and 12, in case only sample tubes 502 with large diameter are loaded into the universal tray insert 200 in an optimized way, up to 21 large diameter sample tubes 501, such as PreservCyt tubes, can fit in the universal tray 200. Moreover, as shown in FIGS. 13 and 14, in case only sample tubes 502 with middle sized diameter are loaded into the universal tray insert 200 in an optimized way, up to 32 middle sized diameter sample tubes 502, such as SurePath tubes, can fit in the universal tray 200. Finally, as shown in FIGS. 15 and 16, in case only sample tubes 503 with small diameter are loaded into the universal tray insert 200 in an optimized way, up to 78 small diameter sample tubes 502, such as PCR tubes, can fit in the universal tray 200. Moreover, as can also be gathered from, for example, FIG. 16, the universal tray insert 200 comprises a color indicator groove 230 provided in order to leave out the space required for the stud hole in the one of the corner posts 104 of the base module 100 comprising the color indicator 107. Here, on the opposite corner of the universal tray insert 200, another color indicator groove 230 is provided, which renders it irrelevant how the universal tray insert 200 is actually inserted into the inner side of the base module 100, since it is also can be inserted in a 180°-turned-around manner.

Figure 17:
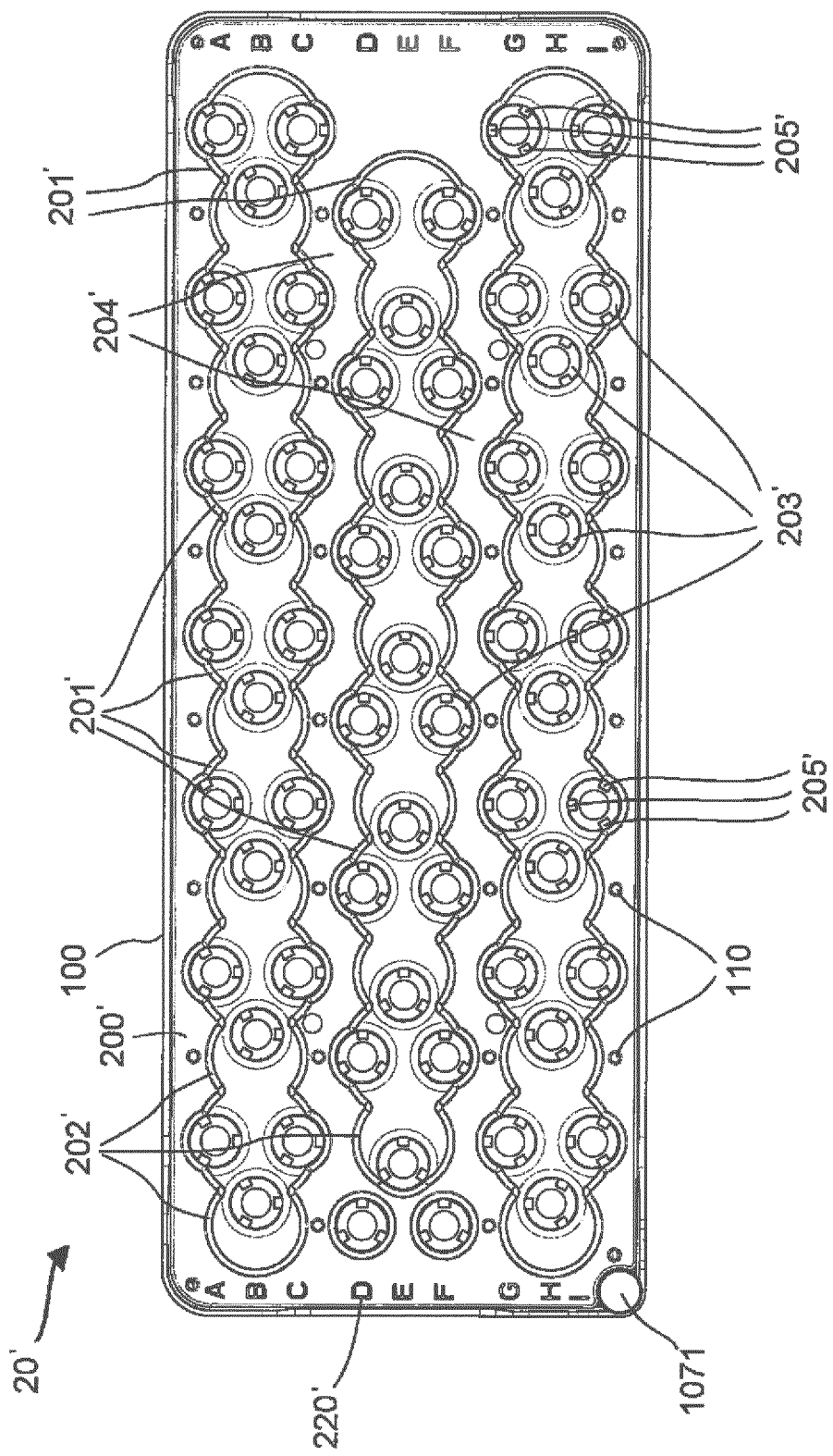
FIG. 17 is a top view of a an alternative embodiment of a multipurpose tray as shown in FIGS. 3 and 4.

In FIG. 17, an alternative multipurpose tray 20' is shown in full in a top view, similar to the illustration of the partially shown multipurpose tray 20 of FIG. 6, comprising the above described base module 100, with an alternative empty universal tray insert 200' inserted therein, without any sample tubes arranged in the alternative universal tray insert 200'. Here, it is to be noted that the universal tray insert 200' can also be provided in one single piece inserted into the base module 100, but the universal tray insert 200' can also be provided in the form of two or more pieces, for easier insertion, which pieces can be attached to each other. The remaining features of the base module 100 of FIG. 17 are identical to the above described base module 100, i.e. the basic structure of the base module 100 is maintained, wherein the application of external features, i.e. the application of writable surfaces 108 or identification codes 109 on the outside of the base module 10 can vary. For example, in the base module 100, a magnet can be provided, for example embedded in the bottom 101 of the base module 100, wherein an automated processing system handling the tray 20', e.g. a tray carrier instrument such as a tray shuttle or the like, can comprise a Hall sensor, which changes its state as soon as the magnet approaches the sensor, i.e. as soon as the tray 20' is loaded. Thereby, the automated processing system can acknowledge the presence of the loaded tray 20'.

As can further be gathered from FIG. 17, the alternative universal tray insert 200' also comprises circular engagement recesses establishing a connection in the form of a releasable push-in connection with the protrusions 110 of the base module 100. Also, similar to the previously described multipurpose tray 20, the alternative multipurpose tray 20' of FIG. 17 comprises fiducial markers 220' provided at the edge of an upper surface of the universal tray insert 200', which fiducial markers 220' are used for clear allocation of each of the tube receiving recesses in the universal tray insert 200' and can be provided in the form of a grid consisting of alphabetic characters and/or numbers, for identifying each tube receiving recess in the universal tray insert 200'. Here, in the alternative embodiment as depicted in FIG. 17, the fiducial markers 220' designating the rows of tube receiving recesses are shown in capital letters A to I.

Regarding the structure of tube receiving recesses in the alternative universal tray insert 200' of the presently described alternative embodiment, there are several different kinds of tube receiving recesses provided as a tube receiving recess array in the alternative universal tray insert 200', wherein the tube receiving recess array in the alternative universal tray insert 200' differs from the tube receiving recess array in the universal tray insert 200. In particular, the array of tube receiving recesses comprises a first group of tube receiving recesses 201' with a large diameter, in order to receive sample tubes with a large outer diameter, such as PreservCyt tubes, a second group of tube receiving recesses 202' with a middle sized diameter, i.e. a smaller diameter compared to the tube receiving recesses 201', in order to receive sample tubes with a middle sized outer diameter, such as SurePath tubes, and a third group of tube receiving recesses 203' with a small diameter, i.e. an even smaller diameter compared to the other tube receiving recesses 201', 202', in order to receive sample tubes with a small outer diameter, such as PCR tubes. As described above, the size of a tube receiving recess 201' of the first group, the size of a tube receiving recess 202' of the second group and the size of a tube receiving recess 203' of the third group differ from each other, i.e. the recess sizes between those groups are different to each other. Moreover, a contour of an inner circumference of each tube receiving recess 201' of the first group intersects with a contour of an inner circumference of at least one adjacent tube receiving recess 202' of the second group. Here, as contour of a tube receiving recess inner circumference, an outline of the tube receiving recess inner circumference is to be understood, wherein the contour or outline of the tube receiving recess inner circumference can also be identified as the substantial cross-section of the respective tube receiving recess when viewed from above. However, as can also be gathered from FIG. 17, the inner circumferences of the tube receiving recesses 201', 202' of both the first group and the second group are not continuous, since the tube receiving recesses 201', 202' of both groups intersect with each other, thus exhibiting an intersection of the contour of a tube receiving recess inner circumference of the first group of tube receiving recesses 201' with the contour of an inner circumference of at least one adjacent tube receiving recess 202' of the second group of tube receiving recesses 202'. Also, the intersection of contours of the first group of tube receiving recesses 201' and the second group of tube receiving recesses 202' constitutes a non-tangential crossover of contours, meaning that the contour of an inner circumference of each tube receiving recess 201' of the first group crosses the contour of an inner circumference of at least one adjacent tube receiving recess 202' of the second group in a non-tangential manner. Such arrangement of tube receiving recesses 201', 202' specifically assists in achieving a further optimized way of fitting tubes with two differing diameters into the alternative universal tray insert 200', in order to achieve an increase in receivable tube number that can be inserted into the universal tray insert 200'. Here, in view of the alternative embodiment of the universal tray insert 200', it is pointed out that the differing distribution of recesses 201', 202' and 203' has been chosen in order to achieve a further advantage, i.e. that more space is provided for fingers of a sample tube gripper or the like, in order for the same to be able to better grip the tubes that need to be gripped further down, i.e. at a lower position on the outside of the respective sample tube.

As already described above, the tube receiving recess array of the alternative universal tray insert 200' of the alternative multipurpose tray 20' comprises additionally the tube receiving recesses 203' of the third group, in addition to the already described first and second groups of tube receiving recesses 201', 202', wherein a contour of an inner circumference of at least one of tube receiving recesses 203' of the third group can intersect with a contour of an inner circumference of at least one adjacent tube receiving recess 201', 202' of the first and/or second group. Here again, as contour of an inner circumference of a tube receiving recess 203', an outline of the inner circumference of the tube receiving recess 203' is to be understood, wherein the contour or outline of the inner circumference of the tube receiving recess 203' can also be identified as the substantial cross-section of the tube receiving recess 203' when viewed from above. As can be gathered from FIG. 17, within each of the tube receiving recesses 203', tube springs 205' are provided, in order to be able to securely hold tubes with an even smaller cross-section, such as tubes with a cross-section of 12 mm or 14 mm, wherein—in the present embodiment—each tube receiving recess 203' exhibits an exemplary number of three tube springs 205' in order to be able to securely hold a tube with an even smaller cross-section in a centric manner within the recess 203'. Of course, the number of tube springs 205' can also be different, as long as the tube with an even smaller cross-section can be hold in a centric manner. Here, the tube springs 205' are at least in part inserted into the inner circumference of the tube receiving recess 203' so that merely tube contact parts of the tube springs 205' protrude therefrom. Also, a center axis of each respective tube receiving recess 203' of the third group is again arranged in an eccentric manner in relation to the center axis of an adjacent tube receiving recess 201' of the first group and to the center axis of an adjacent tube receiving recess 202' of the second group, similar to the previously described universal tray insert 200, meaning that the center axes of all groups of tube receiving recesses 201', 202', 203' do not coincide with each other. Accordingly, the three differing types of sample tubes 501, 502, 503 with three differing diameters can also fit in the alternative universal tray insert 200' and, thus, in the respective alternative multipurpose tray 20', always in a specifically optimized way, particularly optimized for improved gripping of each tube, in order to achieve an increase in receivable and graspable tube number that can be inserted into the alternative universal tray insert 200'. For example, in case only one of the three different sample tube types is loaded into the alternative universal tray insert 200' of the presently described design as shown in FIG. 17, it becomes possible to load 20 pieces of sample tubes 501 with large diameter, such as PreservCyt tubes, 20 pieces of sample tubes 502 with a middle sized diameter, such as SurePath tubes, or 62 pieces of sample tubes 503 with a small diameter, such as PCR tubes. Thus, the alternative universal tray insert 200' of the presently described alternative embodiment can receive between 20 and 62 sample tubes, of the same type or of different types in a mixed manner, depending on the composition of loaded sample tubes 501, 502, 503.

Regarding the depth of the tube receiving recesses 203' of the third group, it has to be noted that the same are partially provided in the bottom of one or several of the tube receiving recesses 201', 202' of the first and second group, meaning that the depth of the tube receiving recess 203' of the third group is deeper than the depth of the tube receiving recesses 201', 202' of the first and second group, similar to the embodiment of universal tray insert 200 as described before. However, contrary to the embodiment of universal tray insert 200 as described before, the alternative universal tray insert 200' of the presently described alternative embodiment comprises the already mentioned upper surface of the universal tray insert 200', which exhibits the fiducial markers 220', and in which the different tube receiving recesses 201', 202', 203' are provided into the upper surface of the universal tray insert 200' towards the bottom 101 of the base module 100. Thereby, the different depths, different sizes and the eccentric arrangement of the tube receiving recesses 201', 202', 203' are established, wherein the arrangement of tube receiving recesses 201', 202', 203' of the universal tray insert 200' results in an outer circumference of upper surface and two connecting elements in the form of division bars or division bridges 204' instead of the brackets 204 of the universal tray insert 200. Thus, the particular surface structure with protruding brackets 204 is omitted in the universal tray insert 200', resulting in a smooth and substantially continuous upper surface of the universal tray insert 200', of course except for the recesses 201', 202', 203', wherein, in the present case, for the sake of improved utilization of space, additional independent tube recesses 203' are provided into the upper surface of the universal tray insert 200', exemplary shown in FIG. 17 in the form of two additional independent tube recesses 203' on the left side of the illustration.

Figure 18:
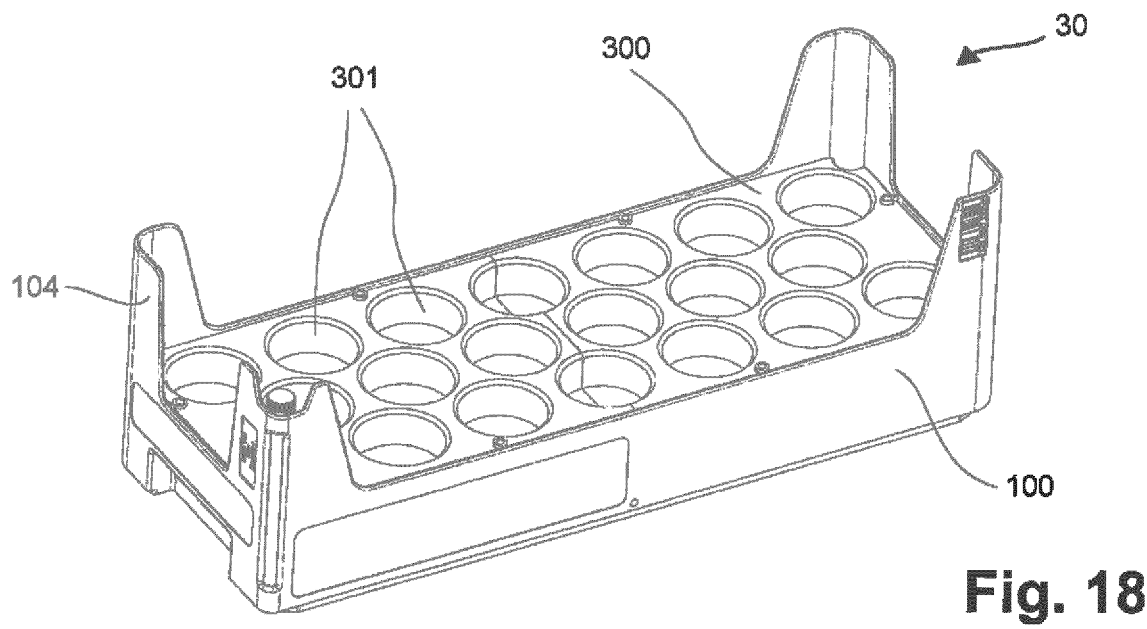
FIG. 18 is a schematic perspective illustration of a multipurpose tray with a tray insert for urine sample containers inserted therein, as also shown in FIG. 1 in the middle position.

In FIG. 18, as an alternative specific embodiment, the multipurpose tray 30 as depicted in the middle position of FIG. 1 is shown, which comprises the base module 100 as shown in FIG. 2 and as used in correlation with the previously described universal tray inserts 200, 200' and in which a urine sample tray insert 300 for urine sample containers is inserted, without any urine sample containers arranged in the urine sample tray insert 300. Here, in order to avoid the repetition of the description of identical features, only the differences vis-à-vis the previously described specific embodiment are described. In particular, the base module 100 is identical to the base module 100 as described in view of FIGS. 1 to 17. Similarly to the universal tray inserts 200, 200' as described above, the urine sample tray insert 300 is inserted into the base module 100 by means of the same tongue-and-groove connection, wherein the urine sample tray insert 300 is shown in a bisected manner, i.e. the urine sample tray insert 300 consists of two halves which are both identical and inserted into the base module 100, see also the color indicator groove at the edge. The urine sample tray insert 300 provides urine sample container recesses 301 for 20 urine sample containers 601, see also FIG. 19, in which two multipurpose trays 30 are stacked on top of each other. Here again, corner posts 104 generate sufficient distance between the closed bottom 101 and the open upper side for the base module 100 to be able to receive the urine sample tray insert 300 as well as the respective urine sample containers 601 provided therein, without interacting with the other base module 100 stacked on top of it.

Figure 20:
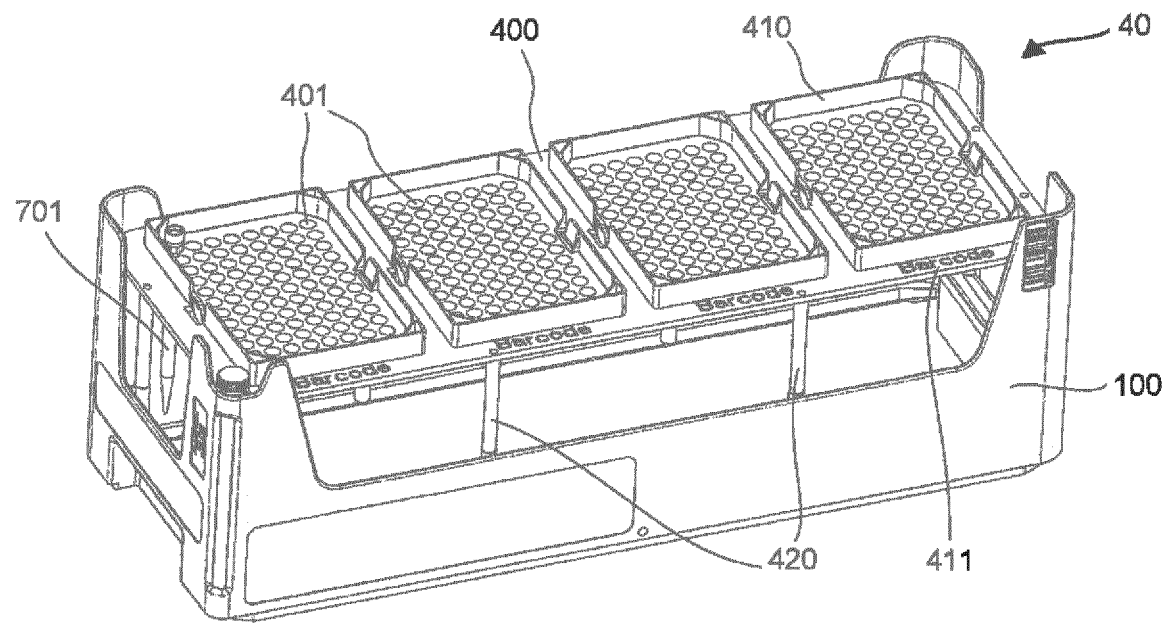
FIG. 20 is a schematic perspective illustration of a multipurpose tray with several tray inserts inserted therein, each tray insert consisting of a tip rack for receiving consumable pipette tips, as also shown in FIG. 1 on the right side.
Figure 21:
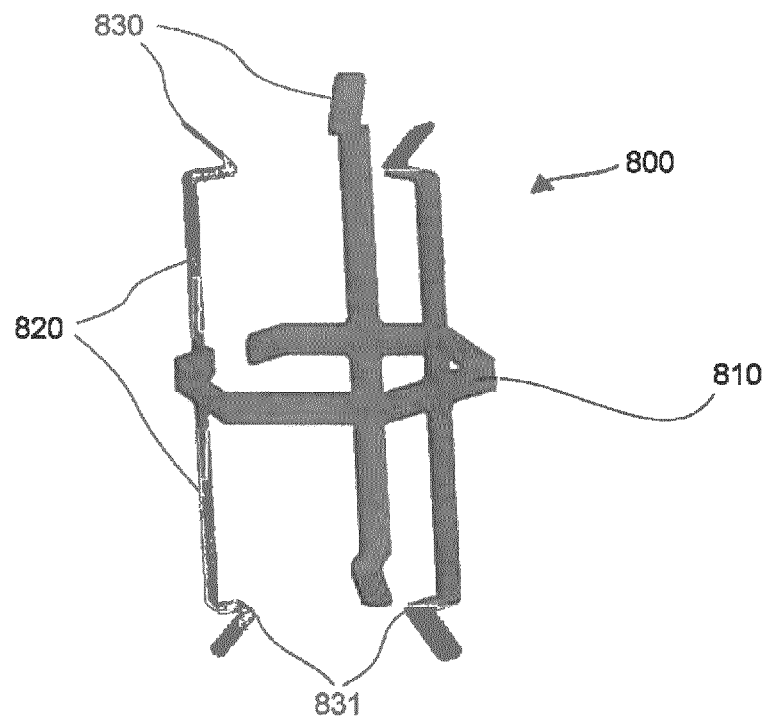
FIG. 21 is an enlarged schematic perspective illustration of a centering spring for a universal tray insert according to an embodiment of the present invention.

In FIG. 20, as a further alternative specific embodiment, the multipurpose tray 40 as arranged on the right side of FIG. 1 is shown, comprising a base module 100 as shown in FIG. 2 and as used in correlation with the previously described universal tray inserts 200, 200', 300, and in which a tip rack tray insert 400 with four tip racks 410 inserted therein is shown, wherein one consumable pipette tip 701 is arranged in a tip rack hole 401 or tip rack opening in one of the tip racks of the tip rack tray insert 400 as exemplary content. Here, in order to avoid the repetition of the description of identical features, only the differences vis-à-vis the previously described specific embodiment are described. In particular, the base module 100 is identical to the base module 100 as described in view of FIGS. 1 to 19. In contrast to the universal tray inserts 200, 200' and the urine sample tray insert 300 as described above, the tip rack tray insert 400 is not inserted into the base module 100 by means of the tongue-and-groove connection, due to the overly long pipette tips. However, the tip rack tray insert 400 comprises plug connectors 420 provided on the bottom of the tip rack tray insert 400, which plug connectors 420 are implemented in the form of downwardly protruding pins with a portion with reduced diameter on its lower end. Here, the reduced diameter portions of the plug connectors 410 can be removably inserted, i.e. removably plugged, into the center holes of the protrusions 104, which holes are open to the open side of the base module 100 and which are provided to receive the plug connectors 420, thereby establishing a push-in connection as mentioned above, which can be detached again. Further, the four tip racks 410 are inserted into the tip rack tray insert 400 from above by means of a snap-fit connection or the like. Each tip rack 410 provides 96 tip rack holes 401, resulting in an overall loading capacity of the tip rack tray insert 400 of 384 consumable pipette tips Further, as shown in FIG. 20, each tip rack 410 comprises a barcode 411 on one side of the tip rack tray insert 400, as well as a mark on the tip rack tray insert 400, according to which the operator has to load the tip racks 410.

As mentioned before, a centering spring 800 can be provided inside, for example, at least one of the tube receiving recesses 201, 201', 202, 202', 203, 203' for centering and holding a smaller sample tube inside one of the tube receiving recesses 201, 201', 202, 202', 203, 203' in case the respective tube receiving recess 201, 201', 202, 202', 203, 203' has a larger inner diameter than the outer diameter of the sample tube to be held. Accordingly, the centering spring 800 has a similar function as the above mentioned tube spring 205'. Accordingly, such a centering spring 800 can further improve the universal property of the universal tray inserts 200, 200', since the universal tray inserts 200, 200' can be universally used for a greater plurality of different kinds of sample tubes, i.e. exceeding the three differently sized sample tubes 501, 502, 503. Here, as a specific example, the centering spring 800 is made of spring steel and comprises a substantially circular, or hexagonal, middle part 810 for attachment inside a respective tube receiving recess 201, 201', 202, 202', 203, 203', and 3 clamp arms 820 protruding away from the middle part 810 in a longitudinal manner on each side of the middle part 810, each clamp arm 820 comprising an inwardly protruding nib 830 at its end, for contacting the sample tube to be held, thereby holding and centering the same in coaxial manner with the centering spring 800 itself, i.e. with the respective tube receiving recess 201, 201', 202, 202', 203, 203', in a clamped manner. The nib 830 is formed in a V-shape with the pointed end 831 directed inward, as contact point with the sample tube to be held. since at least 3 clamp arms 820 are provided on each side of the middle part 810, a three-point spring support is achieved by the centering spring 800, enabling the centering and holding of a sample tube inside the centering spring 800.

In addition to the above, as further specific embodiments of multipurpose trays to be used for an analyzer, and due to the fact that the base module 100 can exhibit the size of 1×4 SBS (society of biomolecular screening=standard for microplate sizes), an insert with empty microwell plates for further processing can be inserted into the base module 100. Furthermore, an insert for carrying reagents can also be considered, for example in the form of 4 MGP (magnetic glass particle) cassettes provided in the tip rack tray insert 400 instead of the tip racks 410.

Figure 22:
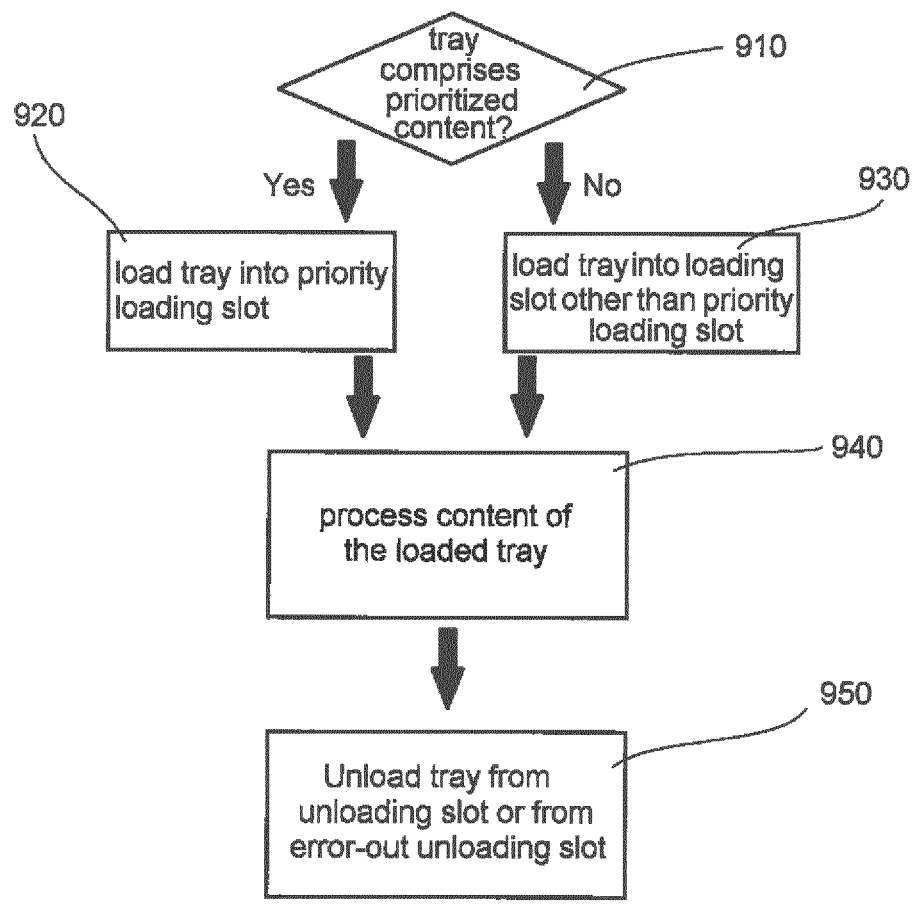
FIG. 22 is a flowchart illustrating an embodiment of a method of the present invention.
Figure 23:
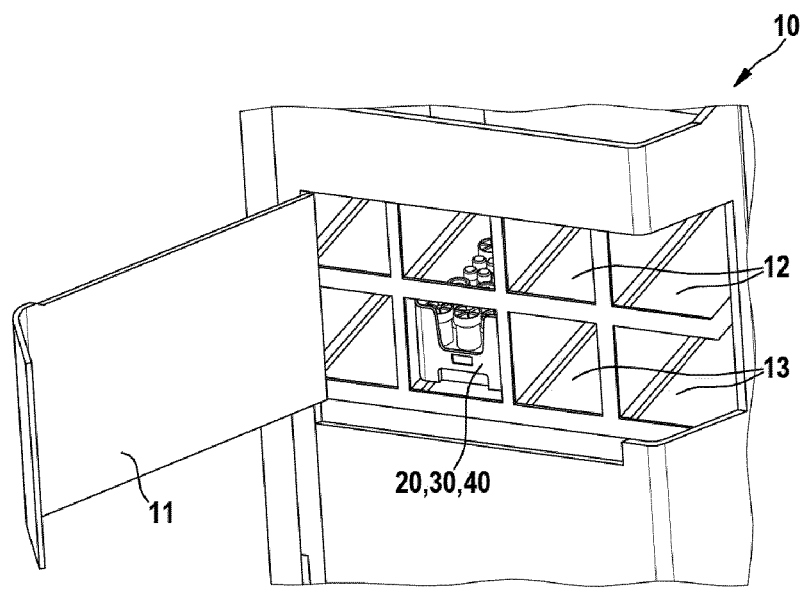
FIG. 23 is a schematic perspective illustration of a loading/unloading station of an automated processing system, for loading/unloading one or several multipurpose trays according to an embodiment of the present invention.
Figure 24:
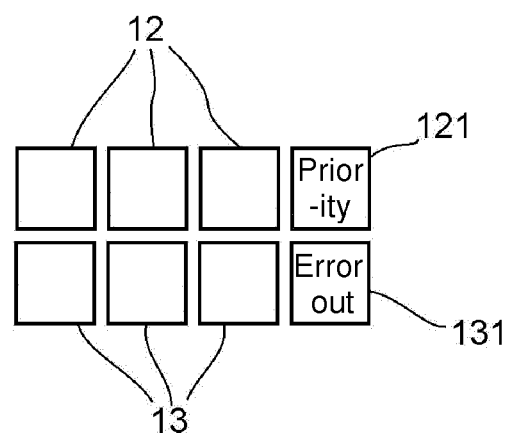
FIG. 24 is a schematic illustration of the arrangement of loading/unloading slots as shown in FIG. 23.

According to a specific embodiment of the present invention, a method of simplified loading/unloading of a multipurpose tray into/from an automated processing system by an operator is shown in FIG. 22. Further, an exemplary loading/unloading station 10 of the automated processing system is shown in FIG. 23, wherein an arrangement of the loading slots 12 and unloading slots 13 of FIG. 23 is shown in FIG. 24 in a more specific embodiment. The loading/unloading station 10 of the automated processing system can comprise a flap door 11 for covering the loading slots 12 and unloading slots 13, if desired, in order to avoid any disturbance of the loaded multipurpose trays, or also of a multipurpose tray to be unloaded, as illustrated in one of the unloading slots 13 in FIG. 23. Here, such a multipurpose tray can be one of the multipurpose trays 20, 20' 30, 40 as described above in detail, or, alternatively, another kind of multipurpose tray having any kind of tray insert inserted in its base module 100, wherein the technical features mentioned in its context in regard to the structure of the multipurpose tray also apply for the method of the present invention and are, thus, not repeated at this point. In further detail, the method comprises the following steps, which can be arranged in the following order in line with the flowchart of FIG. 22:

Decision step 910: Determining if the multipurpose tray 20, 20', 30, 40 to be loaded into a loading slot 12 contains prioritized content.

Execution step 920: In case the determination in decision step 910 results in the multipurpose tray 20, 20', 30, 40 to be loaded into a loading slot 12 containing prioritized content, loading the multipurpose tray 20, 20', 30, 40 into a priority loading slot 121 of the automated processing system by the operator.

Execution step 930: In case the determination in decision step 910 results in the multipurpose tray 20, 20', 30, 40 to be loaded into a loading slot 12 does not contain prioritized content, loading the multipurpose tray 20, 20', 30, 40 into any loading slot 12 other than the priority loading slot 121 of the automated processing system by the operator.

Execution step 940: Processing the content of the loaded multipurpose tray 20, 20', 30, 40 by laboratory instrument of the automated processing system.

Execution step 950: Unloading the multipurpose tray 20, 20', 30, 40 from an unloading slot 13 or from an error-out unloading slot 131 of the automated processing system by the operator.

In regard to the execution step 940, i.e. the step of processing the content of the loaded multipurpose tray 20, 20', 30, 40 by laboratory instrument of the automated processing system, the automated processing system comprises a sensor recognizing the content of the multipurpose tray 20, 20', 30, 40 loaded into one of the loading slots 12 without interaction between the operator and software of the automated processing system, i.e. the automated processing system is able to automatically recognize the loaded multipurpose tray 20, 20', 30, 40 and its content by means of the sensor, such as an optical sensor, an RFID sensor or the like, based on reading, for example, a machine-readable identification code 109 provided on the base module 100 of the multipurpose tray 20, 20', 30, 40. Thus, the automated processing system is able to identify the necessary or desired processing steps to be carried out automatically by the laboratory instruments inside the automated processing system, without the necessity for the operator of data input regarding the content of the multipurpose tray 20, 20', 30, 40, for example by means of a user interface.

In regard to the execution step 950, the multipurpose tray 20, 20', 30, 40 to be unloaded from any unloading slot 13 of the automated processing system can be unloaded by the operator from the respective unloading slot 13 without interaction between the operator and software of the automated processing system regarding the format or content of the multipurpose tray 20, 20', 30, 40, i.e. the automated processing system allows unloading of the multipurpose tray 20, 20', 30, 40 without the necessity for the automated processing system to provide data about the multipurpose tray 20, 20', 30, 40 to be unloaded from any of the unloading slots 13 to the operator, for example by means of a user interface. However, in general, any multipurpose tray 20, 20', 30, 40 to be unloaded from any of the unloading slots 13 of the automated processing system can only be unloaded by the operator by interaction between the operator and software of the automated processing system, i.e. the automated processing system allows unloading of the multipurpose tray 20, 20', 30, 40 to only with a respective input from the operator to the system, for example by means of the user interface. Thus, it is not possible to manually unload the multipurpose tray 20, 20', 30, 40 without interaction between the operator and the software. Only when "unloading" is activated on the user interface, such as a touchscreen, the multipurpose tray 20, 20', 30, 40 can be unloaded, i.e. when an "unlock" button on the touchscreen has been activated, the multipurpose tray 20, 20', 30, 40 is provided automatically to the outside, for example by pushing open the flap door 11 of the loading/unloading station 10.

In general, the automated processing system can comprise a control unit carrying application software for interaction with an operator as well as for controlling the workflow inside the automated processing system. Further, the automated processing system can lock any unloading slot 13 for preventing unloading of the multipurpose tray 20, 20', 30, 40 from the unloading slot 13 before clearance, for example while the respective multipurpose tray 20, 20', 30, 40 is still in the process of processing step 940. Accordingly, while the multipurpose tray 20, 20', 30, 40 is in processing, the automated processing system prevents manual removal of the multipurpose tray 20, 20', 30, 40 from the respective unloading slot 13, for example by means of a manual lock. Alternatively, or additionally, the automated processing system can comprise a loading/unloading status indicator for each slot, for example in the form of a LCD display or the like, indicating the status of loading/unloading permission or loading/unloading prohibition for each slot 12, 13. Here, a loading/unloading status indication can be given, as example, by means of the following signs:

Displayed sign: ↑ (in green color); Meaning: Load multipurpose tray 20, 20', 30, 40; Task: Multipurpose tray 20, 20', 30, 40 can be loaded by the operator.

Displayed sign: ↓ (in green color); Meaning: Unload multipurpose tray 20, 20', 30, 40; Task: Multipurpose tray 20, 20', 30, 40 can be unloaded by the operator.

Displayed sign: ↓ (in red color); Meaning; Unload multipurpose tray 20, 20', 30, 40 (buffer has no more capacity); Task: Multipurpose tray 20, 20', 30, 40 has to be loaded by the operator.

Displayed sign:  ; Meaning; Loading slot 12 and/or unloading slot 13 is locked; Task: No task for the operator.

Accordingly, the presently described method offers a user-convenient way of loading samples and disposables into an automated processing system, wherein the operator can load the multipurpose tray 20, 20', 30, 40 comprising supplies and/or samples into any one of the loading slots 12, without having to identify a loading slot matching the format of content of the multipurpose tray 20, 20', 30, 40 to be loaded each time a multipurpose tray 20, 20', 30, 40 has to be loaded into the automated processing system.

In the presently described method, the loading/unloading station 10 of the automated processing system is particularly equipped with 8 loading/unloading slots 12, 13 as tray interface between the outside and the inside of the automated processing system, wherein the slots 12, 13 are arranged in two rows of slots 12, 13, with 4 loading slots 12 on top and 4 unloading slots 13 at the bottom. Here, as illustrated in FIG. 24, the loading slot 12 on the right can be designated to be a priority loading slot 121, wherein the automated processing system carries out the processing step 940 with prioritizing the multipurpose tray 20, 20', 30, 40 with prioritized content loaded into the priority loading slot 121.

Regarding the execution step 950 of unloading the multipurpose tray 20, 20', 30, 40 from an unloading slot 13 or from an error-out unloading slot 131 of the automated processing system by the operator, different kinds of multipurpose trays 20, 20', 30, 40 with differing contents can be unloaded from the unloading slots 13. However, one of the unloading slots 13 can be designated to be an unloading slot for unloading sample error trays, i.e. an error-out unloading slot 131, from which multipurpose trays 20, 20', 30, 40 with sample tubes that have been identified by the automated processing system to exhibit some kind of error, such as an unreadable label or the like, or also in case of an erroneous sample, are to be unloaded. Accordingly, the execution step 950 of unloading the multipurpose tray 20, 20', 30, 40 can comprise unloading of the multipurpose tray 20, 20', 30, 40 with predetermined content from a predetermined unloading slot in the form of the error-out unloading slot 131, wherein the predetermined content can be containers with erroneous samples.

While the current invention has been described in relation to its specific embodiments, it is to be understood that this description is for illustrative purposes only. Accordingly, it is intended that the invention be limited only by the scope of the claims appended hereto. Various publications are cited herein, the disclosures of which are incorporated by reference in their entireties.

The invention claimed is:

1. A base module for a multipurpose tray for an automated processing system,
the base module comprising a rectangular structure with an open upper side, a substantially closed bottom side and side walls with a respective open slot, wherein each corner of the rectangular structure comprises an angular cornerpost, and wherein the base module is stackable on top of a second base module identical to the base module,
wherein the base module comprises protrusions protruding laterally inward towards an inner side of the base module, for snap connection engagement with at least one tray insert, said at least one tray insert being releasably engagable within said open side of the base module by engagement with the protrusions of the base module;
wherein the base module further comprises at least one manually operable color indicator for indication of a loading status of a content of the multipurpose tray, the color indicator comprising a rotating indicator pole provided in a pocket of a corner post of the base module, wherein the pocket comprises a viewing window viewable from outside of the base module, wherein the rotating indicator pole is configured to display different colors through the viewing window when rotated.

2. The base module according to claim 1, wherein each protrusion protruding laterally inwards toward the inner side of the base module comprises a center hole.

3. The base module according to claim 1, wherein the bottom side of the base module comprises a step portion with a reduced perimeter, the step portion matching into an upper edge of the open side of the second base module.

4. The base module according to claim 1, wherein the base module comprises at least one handle on its perimeter for improved transportability of the base module by an operator.

5. The base module according to claim 1, wherein the base module comprises two handles on its perimeter opposite to each other for improved transportability of the base module by an operator.

6. The base module according to claim 1, wherein the base module comprises at least one engagement indentation on its perimeter for improved transportability of the base module by a tray carrier of the automated processing system.

7. The base module according to claim 6, wherein the at least one engagement indentation is provided within a handle positioned on the base module's perimeter.

8. The base module according to claim 1, wherein the base module comprises two engagement indentations on its perimeter opposite to each other for improved transportability of the base module by a tray carrier of the automated processing system.

9. The base module according to claim 8, wherein each engagement indentation is provided within a handle allocated on the base module's perimeter.

10. The base module according to claim 1, wherein the base module comprises at least one writable surface on its perimeter configured to display removable markings applied by a human operator, wherein the at least one writable surface comprises a whiteboard material.

11. The base module according to claim 1, wherein the base module comprises at least one identification code on its perimeter.

12. The base module according to claim 1, wherein the base module comprises a magnet for Hall sensor application embedded in a bottom of the base module.

13. The base module according to claim 1, wherein the base module is an injection molded component.

14. The base module according to claim 13, wherein the base module is made of PC/SAN, PC/ABS or PP.

* * * * *